(12) United States Patent
Civin et al.

(10) Patent No.: US 9,918,972 B2
(45) Date of Patent: Mar. 20, 2018

(54) TREATMENT OF LEUKEMIA WITH ARTEMISININ DERIVATIVES AND COMBINATIONS WITH OTHER ANTINEOPLASTIC AGENTS

(71) Applicant: UNIVERSITY OF MARYLAND, BALTIMORE, Baltimore, MD (US)

(72) Inventors: Curt Civin, Baltimore, MD (US); Xiaochun Chen, Timonium, MD (US); Jennifer Fox, Falls Church, VA (US); Gary Posner, Baltimore, MD (US); Michelle Rudek, Fulton, MD (US)

(73) Assignees: THE UNIVERSITY OF MARYLAND, BALTIMORE, Baltimore, MD (US); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/757,433

(22) Filed: Dec. 23, 2015

(65) Prior Publication Data

US 2016/0175331 A1 Jun. 23, 2016

Related U.S. Application Data

(60) Provisional application No. 62/096,077, filed on Dec. 23, 2014, provisional application No. 62/238,468, filed on Oct. 7, 2015.

(51) Int. Cl.

| *A61K 31/44* | (2006.01) |
|---|---|
| *A61K 31/357* | (2006.01) |
| *A61K 31/7068* | (2006.01) |
| *A61K 31/704* | (2006.01) |
| *A61K 31/7048* | (2006.01) |
| *A61K 45/06* | (2006.01) |
| *A61K 31/282* | (2006.01) |
| *A61K 31/475* | (2006.01) |
| *A61K 31/675* | (2006.01) |

(52) U.S. Cl.
CPC .......... *A61K 31/44* (2013.01); *A61K 31/282* (2013.01); *A61K 31/357* (2013.01); *A61K 31/475* (2013.01); *A61K 31/675* (2013.01); *A61K 31/704* (2013.01); *A61K 31/7048* (2013.01); *A61K 31/7068* (2013.01); *A61K 45/06* (2013.01)

(58) Field of Classification Search
None
See application file for complete search history.

(56) References Cited

U.S. PATENT DOCUMENTS

| 7,989,491 | B2 * | 8/2011 | Schlegel | A61K 31/335 |
|---|---|---|---|---|
| | | | | 514/450 |
| 2006/0084675 | A1 * | 4/2006 | Efferth | A61K 31/47 |
| | | | | 514/310 |
| 2010/0279976 | A1 * | 11/2010 | Wang | A61K 31/357 |
| | | | | 514/49 |
| 2011/0152289 | A1 * | 6/2011 | Begue | C07D 519/00 |
| | | | | 514/254.11 |
| 2012/0108545 | A1 * | 5/2012 | Posner | C07D 519/00 |
| | | | | 514/63 |
| 2012/0258181 | A1 * | 10/2012 | Pisano | A61K 31/24 |
| | | | | 424/649 |
| 2013/0136757 | A1 * | 5/2013 | Dalgleish | A61K 31/282 |
| | | | | 424/184.1 |
| 2015/0031677 | A1 * | 1/2015 | Posner | C07D 493/18 |
| | | | | 514/211.13 |
| 2015/0183798 | A1 * | 7/2015 | Posner | C07D 493/08 |
| | | | | 514/211.1 |
| 2015/0361088 | A1 * | 12/2015 | Posner | A61K 31/357 |
| | | | | 514/100 |

OTHER PUBLICATIONS

Mott, B. T., He, R., Chen, X., Fox, J. M., Civin, C. I., Arav-Boger, R., & Posner, G. H. (2013). Artemisinin-derived dimer phosphate esters as potent anti-cytomegalovirus (anti-CMV) and anti-cancer agents: A structure-activity study. Bioorganic & medicinal chemistry, 21(13), 3702-3707.*
Davids, M. S., & Letai, A. (2012). Targeting the B-cell lymphoma/leukemia 2 family in cancer. Journal of Clinical Oncology, 30(25), 3127-3135.*
Pratz, K. W., Sato, T., Murphy, K. M., Stine, A., Rajkhowa, T., & Levis, M. (2010). FLT3-mutant allelic burden and clinical status are predictive of response to FLT3 inhibitors in AML. Blood, 115(7), 1425-1432.*
Locatelli, F., Testi, A. M., Bernardo, M. E., Rizzari, C., Bertaina, A., Merli, P., . . . & Zecca, M. (2009). Clofarabine, cyclophosphamide and etoposide as single-course re-induction therapy for children with refractory/multiple relapsed acute lymphoblastic leukaemia. British journal of haematology, 147(3), 371-378.*
Souers, A. J., Leverson, J. D., Boghaert, E. R., Ackler, S. L., Catron, N. D., Chen, J., . . . & Huang, D. C. (2013). ABT-199, a potent and selective BCL-2 inhibitor, achieves antitumor activity while sparing platelets. Nature medicine, 19(2), 202-208. (Year: 2013).*
Oltersdorf, T., Elmore, S. W., Shoemaker, A. R., Armstrong, R. C., Augeri, D. J., Belli, B. A., . . . & Joseph, M. K. (2005). An inhibitor of Bcl-2 family proteins induces regression of solid tumours. Nature, 435(7042), 677-681. (Year: 2005).*

(Continued)

*Primary Examiner* — Shaojia A Jiang
*Assistant Examiner* — Dale R Miller
(74) *Attorney, Agent, or Firm* — Wenderoth, Lind & Ponack, L.L.P.

(57) ABSTRACT

Methods of treating cancer, such as leukemia, via administration of therapeutically effective amounts of artemisinins and second agents are detailed herein. The artemisinins include artesunate, dihydroartemisinin, artemether, arteether, artelinate, and ART-838. The second agents include BCL-2 inhibitors such as ABT-199, ABT-263, and ABT-737; kinase inhibitors such as lestaurtinib, midostaurin, and sorafenib; and anti-neoplastic agents such as cytarabine, doxorubicin, etoposide, cyclophosphamide, triplotide, vinorelbine, cisplatin, and rituximab.

7 Claims, 23 Drawing Sheets

(56) References Cited

OTHER PUBLICATIONS

Misaghian N et al.: "Targeting the leukemic stem cell: the Holy Grail of leukemia therapy", Leukemia, vol. 23(1): pp. 25-42, (2009).
Warner J K et al.: "Concepts of human leukemic development", Oncogene, vol. 23(43): pp. 7164-7177, (2004).
Grunwald M R et al.: "FLT3 inhibitors for acute myeloid leukemia: a review of their efficacy and mechanisms of resistance", Int J Hematol, vol. 97(6): pp. 683-694, (2013).
Ho W E et al.: "Artemisinins: pharmacological actions beyond anti-malarial", Pharmacology & Therapeutics, vol. 142(1): pp. 126-139, (2014).
Mott B T et al.: "Artemisinin-Derived Dimer Phosphate Esters as Potent Anti-Cytomegalovirus (Anti-CMV) and Anti-Cancer Agents: A Structure-Activity Study", Bioorg Med Chem., vol. 21(13): pp. 3702-3707, (2013).
Crespo-Ortiz M P et al.: "Antitumor Activity of Artemisinin and Its Derivatives: From a Well-Known Antimalarial Agent to a Potential Anticancer Drug", Journal of Biomedicine and Biotechnology, vol. 2012: pp. 1-19, (2012).
Posner G H et al.: "Orally Active, Antimalarial, Anticancer, Artemisinin-Derived Trioxane Dimers with High Stability and Efficacy", J. Med. Chem., vol. 46(6): pp. 1060-1065, (2003).
Paik I H et al.: "Second Generation, Orally Active, Antimalarial, Artemisinin-Derived Trioxane Dimers with High Stability, Efficacy, and Anticancer Activity", J. Med. Chem., vol. 49(9): pp. 2731-2734, (2006).
Posner G H. et al.: "Trioxane Dimers Have Potent Antimalarial, Antiproliferative and Antitumor Activities In Vitro", Bioorganic & Medicinal Chemistry, vol. 5(7): pp. 1257-1265, (1997).
Posner G H et al.: "Antimalarial, Antiproliferative, and Antitumor Activities of Artemisinin-Derived, Chemically Robust, Trioxane Dimers", Journal of Medical Chemistry, vol. 42(21): pp. 4275-4280, (1999).
Posner G H et al.: "New Chemical and Biological Aspects of Artemisinin-Derived Trioxane Dimers", Bioorganic & Medicinal Chemistry, vol. 10(1), pp. 227-232, (2002).
Posner G H et al.: "Anticancer and Antimalarial Efficacy and Safety of Artemisinin-Derived Trioxane Dimers in Rodents", J. Med. Chem., vol. 47(5): pp. 1299-1301, (2004).
He R et al.: "An Artemisinin-Derived Dimer Has Highly Potent Anti-Cytomegalovirus (CMV) and Anti-Cancer Activities", PLoS ONE, vol. 6(8): pp. 1-6, (2011).
Chaturvedi D et al.: "Artemisinin and its derivatives: a novel class of anti-malarial and anti-cancer agents", Chemical Society Reviews, vol. 39(2), pp. 435-454, (2010).
Rosenthal A S et al.: "Malaria-Infected Mice Are Cured by a Single Oral Dose of New Dimeric Trioxane Sulfones Which Are Also Selectively and Powerfully Cytotoxic to Cancer Cells", J. Med. Chem., vol. 52(4): pp. 1198-1203, (2009).
Alagbala A A et al.: "Biological Mechanisms of Action of Novel C-10 Non-Acetal Trioxane Dimers in Prostate Cancer Cell Lines", J. Med. Chem., vol. 49(26): pp. 7836-7842, (2006).
Jeyadevan J P et al.: "Antimalarial and Antitumor Evaluation of Novel C-10 Non-Acetal Dimers of 10β-(2-Hydroxyethyl)deoxoartemisinin", J. Med. Chem., vol. 47(5): pp. 1290-1298, (2004).

Efferth T et al.: "The anti-malarial artesunate is also active against cancer", International Journal of Oncology, vol. 18(4): pp. 767-773, (2001).
Dell'Eva R et al.: "Inhibition of angiogenesis in vivo and growth of Kaposi's sarcoma xenograft tumors by the anti-malarial artesunate", Biochemical Pharmacology, vol. 68(12), pp. 2359-2366, (2004).
Efferth T et al.: "Artesunate Induces ROS-Mediated Apoptosis in Doxorubicin-Resistant T Leukemia Cells", PLoS ONE, vol. 2(8): pp. 1-8.
Du J H et al.: "Artesunate induces oncosis-like cell death in vitro and has antitumor activity against pancreatic cancer xenografts in vivo", Cancer Chemother Pharmacol, vol. 65(5): pp. 895-902, (2010).
Ma H et al.: "The Effects of Artesunate on the Expression of EGFR and ABCG2 in A549 Human Lung Cancer Cells and a Xenograft Model", Molecules, vol. 16(12), pp. 10556-10569, (2011).
Xu Q et al.: "Artesunate inhibits growth and induces apoptosis in human osteosarcoma HOS cell line in vitro and in vivo", J Zhejiang Univ-Science B (Biomedicine & Biotechnology), vol. 12(4): p. 247-255, (2011).
Zhou X et al.: "Artesunate inhibits the growth of gastric cancer cells through the mechanism of promoting oncosis both in vitro and in vivo", Anticancer Drugs, vol. 24(9): p. 920-927, (2013).
Jin M et al.: "In vivo study of effects of artesunate nanoliposomes on human hepatocellular carcinoma xenografts in nude mice", Drug Delivery, vol. 20(3-4): pp. 127-133, (2013).
Hooft van Huijsduijnen R et al.: "Anticancer Properties of Distinct Antimalarial Drug Classes", PLoS ONE, vol. 8(12): pp. 1-11, (2013).
Zhang, Z Y et al.: "Artesunate combined with vinorelbine plus cisplatin in treatment of advanced non-small cell lung cancer: A randomized controlled trial", Journal of Chinese Integrative Medicine, vol. 6(2): pp. 134-138, (2008).
Holohan C et al.: "Cancer drug resistance: an evolving paradigm", Nature Reviews Cancer, vol. 13(10): pp. 714-726, (2013).
Crystal A S et al.: "Patient-derived Models of Acquired Resistance Can Identify Effective Drug Combinations for Cancer", Science, vol. 346(6216): pp. 1480-1486, (2014).
Axelrod M et al.: "Combinatorial drug screening identifies compensatory pathway interactions and adaptive resistance mechanisms", Oncotarget, vol. 4(4): pp. 622-635, (2013).
Zhou T et al.: "Combinatorial drug screening identifies synergistic co-targeting of Bruton's tyrosine kinase and the proteasome in mantle cell lymphoma", Leukemia, vol. 28(2): pp. 407-710, (2013).
Roller D et al.: "Synthetic lethal screening with small molecule inhibitors provides a pathway to rational combination therapies for melanoma", Mol Cancer Ther., vol. 11(11): pp. 2505-2515, (2012).
Tyner J W et al.: "Kinase Pathway Dependence in Primary Human Leukemias Determined by Rapid Inhibitor Screening", Cancer Res., vol. 73(1): pp. 285-296, (2013).
Hu S et al.: "Activity of the Multikinase Inhibitor Sorafenib in Combination With Cytarabine in Acute Myeloid Leukemia", J Natl Cancer Inst, vol. 103(11): pp. 893-905, (2011).
Sieber S et al.: "Combination treatment of malignant B cells using the anti-CD20 antibody rituximab and the anti-malarial artesunate", International Journal of Oncology, vol. 35(1): pp. 149-158, (2009).

\* cited by examiner

Artemisinin

Artesunate (AS)

Dihydroartemisinin (DHA)

ART-838

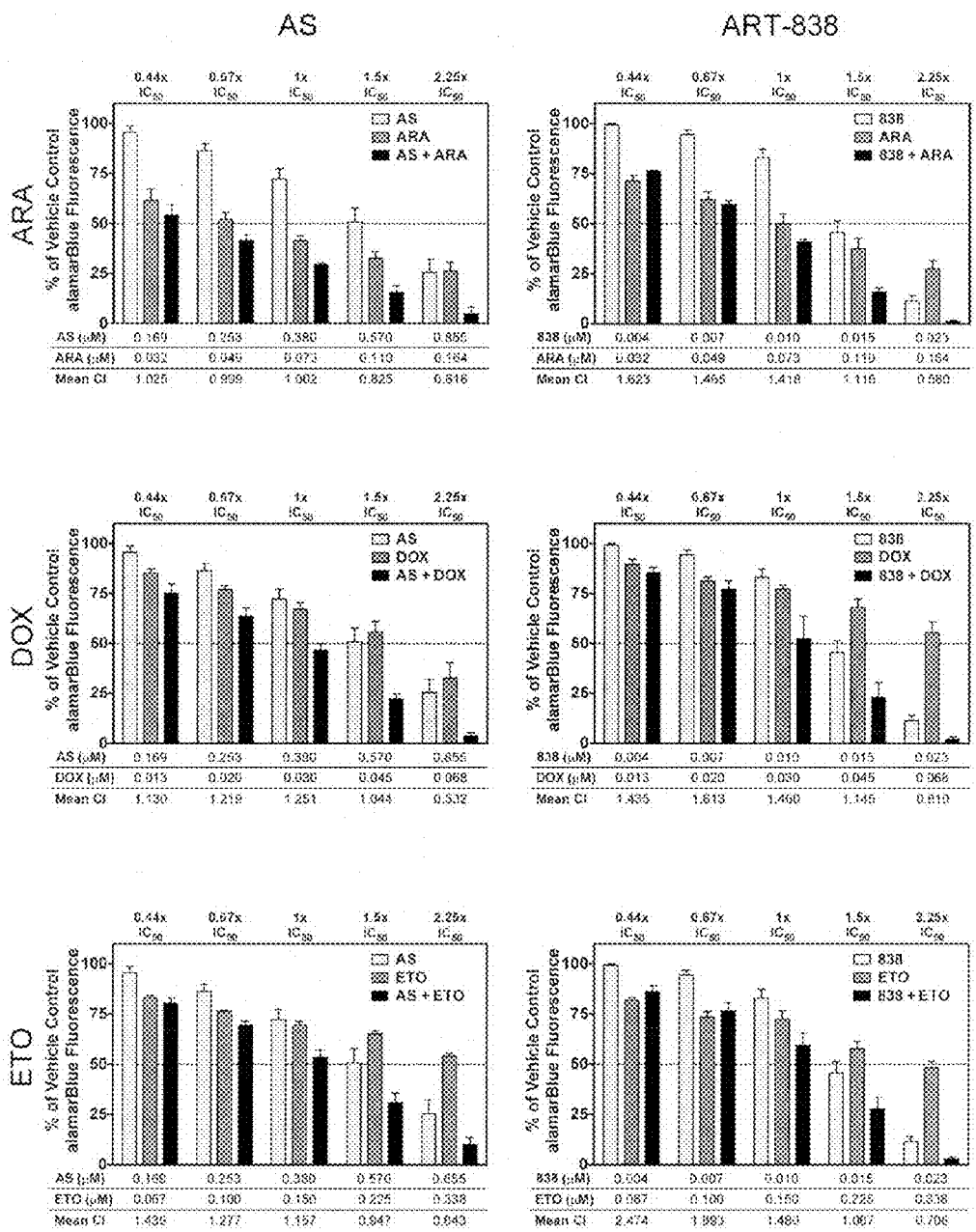

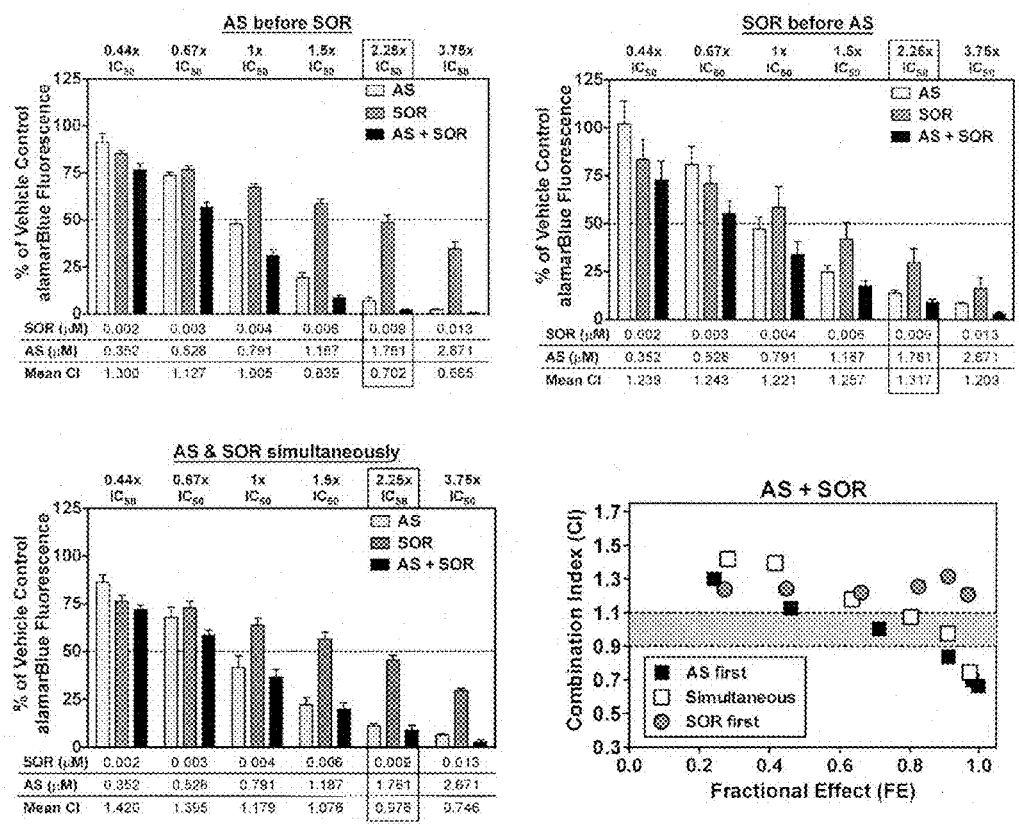

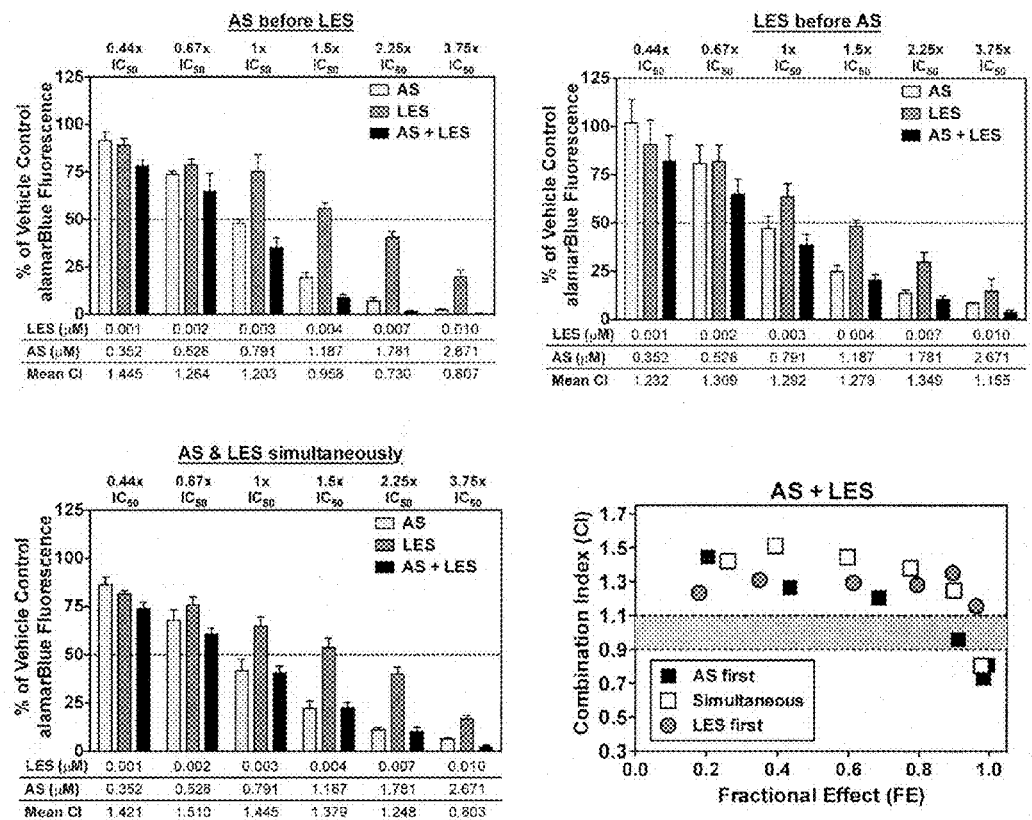

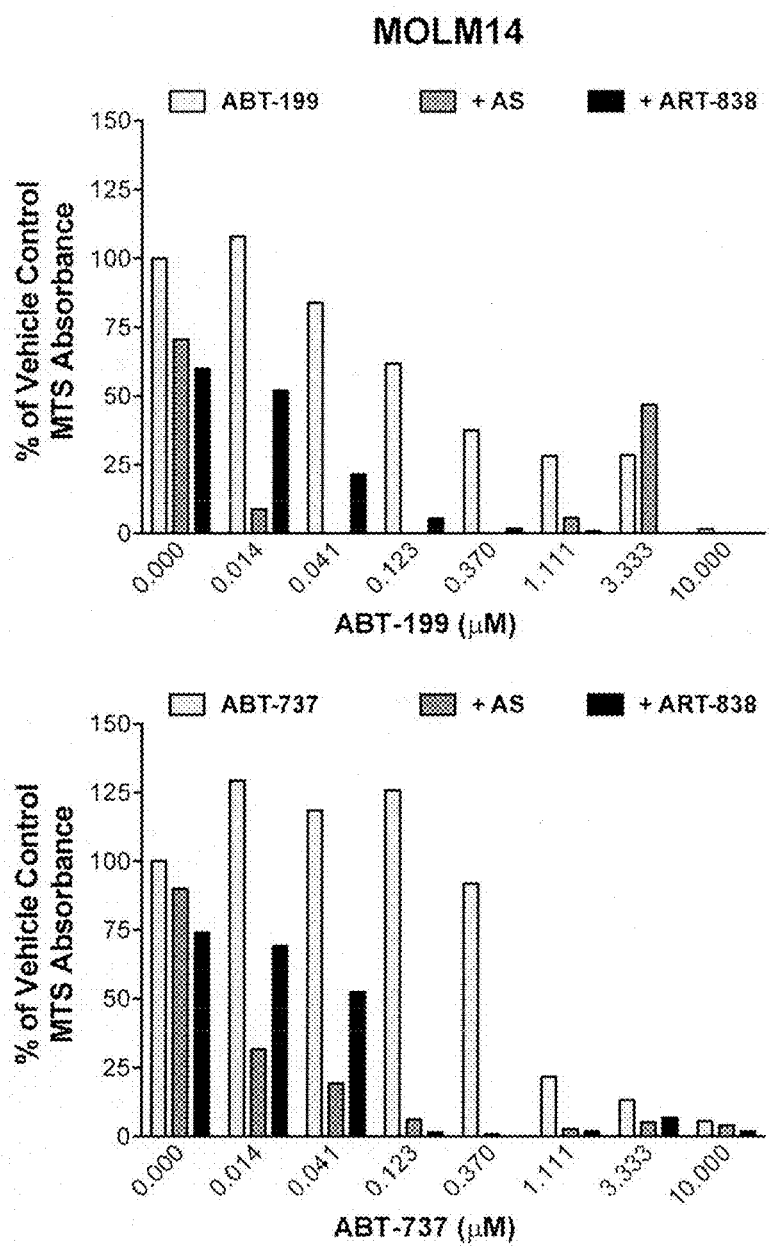

US 9,918,972 B2

TREATMENT OF LEUKEMIA WITH ARTEMISININ DERIVATIVES AND COMBINATIONS WITH OTHER ANTINEOPLASTIC AGENTS

STATEMENT OF FEDERALLY SPONSORED RESEARCH AND DEVELOPMENT

This invention was made with government support under Grant Numbers CA154274, CA070970 and AI034885 awarded by The National Institutes of Health. The government has certain rights in the invention.

BACKGROUND OF INVENTION

The treatment of certain types of cancer can be hindered by the development of resistance in the cancer cells to anti-cancer agents targeted to the cells. Rational drug combinations offer a therapeutic opportunity to avoid development of drug resistance to targeted therapies by simultaneously targeting both the primary target and compensatory pathway(s), preventing activation of pro-survival signaling [39,40]. For example, upregulation of BCL2 or MCL1 has been shown to confer FLT3-independence to leukemia cells [4]. Simultaneous targeting of FLT3 and BCL2 or MCL1, or causing BCL2 or MCL1 down regulation, may produce a lethal effect.

Several lethal drug combination screens have recently identified rational drug combinations based on adaptive resistance mechanisms of cancer cells, such as activation of compensatory signaling pathways [40-43]. Another recent screen used a library of small molecule kinase inhibitors to identify signaling pathway dependencies in primary acute leukemia patient cells, based on inclusion of the common targets of kinase inhibitors to which the sample was sensitive and exclusion of the targets of inhibitors to which the sample was not sensitive [44].

Recent reports have demonstrated that the potent antimalarial drug artemisinin and its semisynthetic derivatives have the potential to be repurposed for use in anti-leukemic regimens. Two artemisinin derivatives, Artesunate (AS) and artemisinin-derived trioxane diphenylphosphate dimer 838 (ART-838), have demonstrated antineoplastic activity in both in vitro and in vivo studies [9,22,25,27].

Pairing artemisinin or its semisynthetic derivatives with other anti-cancer agents could result in effective treatments for leukemia and related diseases. The present application reports on the results of experimental investigations into such combination therapies and new methods for treating cancer developed therefrom, along with other important matters.

BRIEF SUMMARY OF INVENTION

Provided herein are novel drug combinations comprising artemisinins and second agents. These combinations can be used in the treatment of cancer, such as leukemia.

In a first embodiment, the present invention is drawn to methods of treating cancer in a subject, comprising administering therapeutically effective amounts of an artemisinin and a second agent to a subject having cancer. The artemisinin and the second agent may be administered in either order, sequentially or concurrently, with overlapping or non-overlapping periods of administration.

In a second embodiment, the present invention is drawn to methods of treating cancer in a subject, comprising concurrently administering therapeutically effective amounts of an artemisinin and a second agent to a subject having cancer.

In a third embodiment, the present invention is drawn to methods of treating cancer in a subject, comprising sequentially administering therapeutically effective amounts of an artemisinin and a second agent to a subject having cancer.

In each of the embodiments of the invention, the artemisinin and the second agent (i.e., the drugs) may be formulated in pharmaceutical compositions comprising one or both of the drugs and a pharmaceutically acceptable carrier or diluent.

In each of the embodiments of the invention, the artemisinin and the second agent may be administered via the same or different modes of administration.

In certain aspects of each embodiment, the combination of the artemisinin and the second agent have an additive therapeutic effect on the cancer. In other aspects of each embodiment, the combination of the artemisinin and the second agent have a synergistic therapeutic effect on the cancer.

In certain aspects of each embodiment, the artemisinin and the second agent are administered to the subject in the same pharmaceutical composition and via the same mode of administration.

In each embodiment and aspect of the invention, the artemisinin is one or more artemisinins selected from the group consisting of artesunate (AS), dihydroartemisinin (DHA), artemether, arteether, artelinate, ART-838, ART-762, ART-851, ART-836, ART-853, ART-855, ART-895, ART-907, and ART-923.

It will be apparent that a number of different combinations of an artemisinin and a second agent may be used when practicing the various embodiments and aspects of the invention. Such combinations include, but are not limited to: the artemisinin is AS and the second agent is ABT-737; the artemisinin is AS and the second agent is ABT-199; the artemisinin is AS and the second agent is ARA; the artemisinin is AS and the second agent is DOX; the artemisinin is AS and the second agent is ETO; the artemisinin is AS and the second agent is MID; the artemisinin is AS and the second agent is LES; and the artemisinin is AS and the second agent is SOR.

Additional combinations include, but are not limited to: the artemisinin is ART-838 and the second agent is ABT-737; the artemisinin is ART-838 and the second agent is ABT-199; the artemisinin is ART-838 and the second agent is ARA; the artemisinin is ART-838 and the second agent is DOX; the artemisinin is ART-838 and the second agent is ETO; the artemisinin is ART-838 and the second agent is MID; the artemisinin is ART-838 and the second agent is LES; and the artemisinin is ART-838 and the second agent is SOR.

In each embodiment and aspect of the invention, the therapeutically effective amount of the artemisinin is between about 0.1 and 100 mg/kg body weight of the subject.

In each embodiment and aspect of the invention, the second agent is one or more agents selected from the group consisting of BCL-2 inhibitors, kinase inhibitors, and antineoplastic agents. In certain aspects, the BCL-2 inhibitor is selected from the group consisting of ABT-199, ABT-263, and ABT-737. In certain aspects, the kinase inhibitor is selected from the group consisting of lestaurtinib (LES), midostaurin (MID), and sorafenib (SOR). In certain aspects, the anti-neoplastic agent is selected from the group consisting of cytarabine (ARA), doxorubicin (DOX), etoposide (ETO), cyclophosphamide, triplotide, vinorelbine, cisplatin, and rituximab.

In a particular aspect, the invention is directed to a method of treating cancer in a subject, comprising concurrently administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have an additive therapeutic effect on the cancer.

In a particular aspect, the invention is directed to a method of treating cancer in a subject, comprising concurrently administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have a synergistic therapeutic effect on the cancer.

In a particular aspect, the invention is directed to a method of treating cancer in a subject, comprising sequentially administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have an additive therapeutic effect on the cancer.

In a particular aspect, the invention is directed to a method of treating cancer in a subject, comprising sequentially administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have a synergistic therapeutic effect on the cancer.

In each embodiment and aspect of the invention, the therapeutically effective amount of the second agent is between about 0.1 and 100 mg/kg body weight of the subject.

In each embodiment and aspect of the invention, the cancer is one or more cancers selected from the consisting of acute myeloid leukemia (AML), acute lymphoid leukemia (ALL), B cell ALL (B-ALL), T cell ALL (T-ALL), chronic myeloid leukemia (CML), chronic lymphoid leukemia (CLL); lymphoma; myeloma; myelodysplastic syndrome; non-small cell lung cancer; pancreatic cancer; gastric cancer; Kaposi's sarcoma; hepatocellular carcinoma; osteosarcoma; laryngeal squamous cell carcinoma; metastatic uveal melanoma; lung and splenic metastases; advanced non-small cell lung cancer; cervical carcinoma; colorectal cancer; breast cancer; prostate cancer; and all other hematologic malignancies and solid cancers including brain cancers.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIGS. 3A-3B. ART-838 or AS enhanced the cytotoxicity of all six antileukemic drugs tested in KOPN8 cells. Drug combination experiments were performed in KOPN8 cells as for MOLM14 cells (FIG. 2) using (FIG. 3A) standard antileukemic drugs (ARA, DOX, or ETO), or (FIG. 3B) kinase inhibitors (LES, MID, or SOR).

(FIG. 4A, FIG. 4C) MOLM14 drug combination data from FIG. 2 at 2.25× the approximate single-drug 48 h IC50s (0.056 μM ART-838, 1.781 μM AS, 0.643 μM ARA, 0.177 μM DOX, 0.544 μM ETO, 0.007 μM LES, 0.025 μM MID, 0.009 μM SOR) only to highlight combination efficacy on proliferation alongside effects on mitochondrial superoxide generation (FIG. 4B, FIG. 4D). CIs were computed as described above. CI<1 indicates synergy, CI=1, additivity, CI>1, antagonism. (FIG. 4B, FIG. 4D) MOLM14 cells were treated with each of the six partner drugs alone or in combination with ART-838 (FIG. 4B) or AS (FIG. 4D) at 2.25× the approximate single-drug 48 h $IC_{50}$s (same doses as in FIG. 4A, FIG. 4C) for 16 h. Cells were then loaded with 5 μM MitoSox for 30 min, washed, and analyzed by flow cytometry for MitoSox fluorescence (indicating mitochondrial superoxide) in the FL2 channel. Mean fluorescence intensity (MFI) was normalized to that of vehicle control (0.5% DMSO) with no pretreatment (100%, lower dotted lines). Upper dotted lines show MFI of ART-838- or AS-treated cells. Error bars represent the SEM of three independent experiments.

FIGS. 6A-6B. Sequence-dependence of AS combined with SOR and sequence-independence of ART-838 combined with SOR. MOLM14 cells were treated with SOR, ART-838 (FIG. 6A), and/or AS (FIG. 6B), alone and in combination at the doses and ratios described in FIG. 2 in the sequences depicted at the bottom of FIG. 5. After 72 h, cytotoxicity was assessed using alamarBlue. Error bars represent the SEM of three independent experiments, each in triplicate. CIs were computed as described above. CI<1 indicates synergy, CI=1, additivity, CI>1, antagonism. CIs were graphed against the fractional effect (FE; the fraction of cells inhibited at each concentration).

FIGS. 7A-7B. Sequence-dependence of AS combined with LES and sequence-independence of ART-838 combined with LES. MOLM14 cells were treated with LES, ART-838 (FIG. 7A), and/or AS (FIG. 7B), alone and in combination at the doses and ratios described in FIG. 2 in the sequences depicted at the bottom of FIG. 5. After 72 h, cytotoxicity was assessed using alamarBlue. Error bars represent the SEM of three independent experiments, each in triplicate. CIs were computed as described above. CIs were graphed against the fractional effect (FE; the fraction of cells inhibited at each concentration). CI<1 indicates synergy, CI=1, additivity, CI>1, antagonism.

FIGS. 9A-9D. MTS absorbance of leukemia cells treated with BCL2 inhibitors combined with artemisinins. Growth of leukemia cell lines treated with ABT-199 or ABT-737 alone or combined with AS or ART-838 for 48 hours was measured by MTS in a synthetic lethal drug combination screen. FIG. 9A—MOLM14 cells; FIG. 9B—Kasumi-1 cells; FIG. 9C—KOPN8 cells; FIG. 9D—RCH-ACV cells. Light grey bars show the effects of ABT-199 or ABT-737 alone. Dark grey bars show the effects of ABT-199 or ABT-737 combined with AS at its approximate $IC_{50}$. Black bars show the effects of ABT-199 or ABT-737 combined with ART-838 at its approximate $IC_{50}$.

DETAILED DESCRIPTION OF THE INVENTION

I. Definitions

Figure 1:
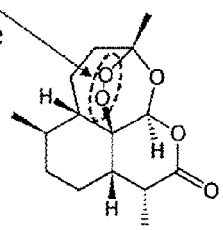
FIG. 1. Structures of artemisinin and its derivatives. Structures of the natural, plant-derived small molecule artemisinin, first-generation derivatives artesunate (AS) and dihydroartemisinin (DHA) (adapted from [8]), and second-generation dimeric derivative ART-838 (adapted from [9]).
Figure 1:
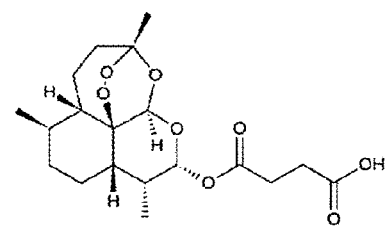
Figure 1:
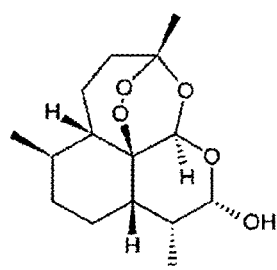
Figure 1:
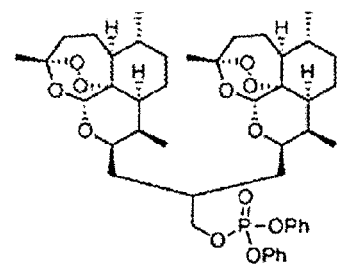

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As reported herein, a synthetic lethal screen of combinations of drugs was undertaken to assess the potential for synergistic interactions between combinations of the artemisinin derivatives artesunate (AS) and ART-838 and a library of targeted inhibitors for use in anti-cancer therapies. The screen assayed the ability of various combinations of the drugs to inhibit the growth of four human cell lines representing acute myeloid leukemia (AML; MOLM14 and Kasumi-1) and B-precursor acute lymphoblastic leukemia (B-ALL; KOPN8 and RCH-ACV). In these screens, both AS and ART-838 synergized with several emerging targeted inhibitors. Particularly strong synergy was observed between either AS or ART-838 and BCL-2 inhibitors (ABT-199, ABT-263, or ABT-737), a class of compounds undergoing active clinical study with high anti-leukemic efficacy. In particular, ABT-199 was recently granted breakthrough therapy designation by the FDA for chronic lymphocytic leukemia.

Investigations into the cellular and molecular mechanism(s) of the observed cooperativity between AS or ART-838 and ABT-199 were undertaken. The synergy of ABT-199 plus AS or ART-838 was validated in low-throughput assays using all four of the noted cell lines. AS and ART-838 are strong inducers of cellular reactive oxygen species (ROS), and BCL-2 family proteins are known to be major downstream players in ROS-mediated apoptosis [61, 62]. As reported herein, it was discovered that AS or ART-838 and ABT-199 cooperatively induced apoptosis, mitochondria ROS, and caspase activity. AS and ART-838 strongly synergized with ABT-199 over a range of low concentrations (4 nM to 1 uM) at which the cell lines were resistant to ABT-199, alone. For example, in the MOLM14 (AML) cell line, while 37 nM of ABT-199 did not inhibit leukemia cell growth, combining the same concentration of ABT-199 together with AS (825 nM, the $IC_{50}$ for AS) or ART-838 (25 nM, the $IC_{50}$ for ART-838) caused 100% growth inhibition.

As also reported herein, similar work was also conducted on combinations of artemisinins and other drugs reported to have some anti-cancer effect, including kinase inhibitors and anti-neoplastic agents. Some of these combinations were also found to demonstrate promising results.

Combinations of artemisinins and these second agents form the basis of the present invention and they may be used in methods of treating subjects having various forms of cancer, as detailed below.

The invention is generally directed to methods of treating cancer in a subject by administering therapeutically effective amounts of the artemisinins and second agents detailed herein to a subject having cancer. As will be evident from the present disclosure, there are a number of different artemisinins that show activity against cancer cells that may be used in these methods. Similarly, there are several different classes of second agents, e.g., BCL-2 inhibitors, kinase inhibitors, and anti-neoplastic agents, that can be used in the combination therapies. Further, the manner in which the drugs (i.e., the artemisinins and the second agents) are administered to a subject may vary, and include administration of the drugs in either order, sequentially or concurrently, with overlapping or non-overlapping periods of administration. It will thus be clear to the skilled person that the methods of the present invention can be practiced with wide latitude and that the scope of the claims is not narrow.

Artemisinins

Artemisinins are rapidly acting antimalarial drugs that are effective against all asexual life stages of the *Plasmodium falciparum* malaria parasite [12]. Artemisinin was first identified in 1972 as the active component of the sweet wormwood plant (*Artemisia annua* L.), used in traditional Chinese medicine to treat fevers (likely caused by malaria) [6]. A 1979 publication by the Qinghaosu Antimalarial Coordinating Research Group demonstrated that artemisinin is a sesquiterpene lactone with an endoperoxide pharmacophore (FIG. 1; a relatively rare pharmacophore among natural compounds) [6,7]. While best known for their antimalarial activity, artemisinins also inhibit growth of a broad range of microbes and cancer cells, especially leukemias [13,27-37]. Akin to the efficacy of the artemisinin artesunate (AS) in multidrug-resistant malaria, AS was as effective against chemotherapy (doxorubicin, hydroxyurea, methotrexate, or vincristine)-resistant CEM (T-ALL) sub-lines as against the parental line [27]. The proven safety profile of the drug in humans makes it an attractive candidate for further study in the treatment of cancer.

Due to the poor solubility and bioavailability of artemisinin, numerous semi- and fully-synthetic derivatives, referred to collectively as "artemisinins" have been developed with improved pharmacological properties [10]. The first generation of artemisinin derivatives includes dihydroartemisinin (DHA; the active metabolite of artemisinin), artesunate (AS; FIG. 1), artemether, arteether, and artelinate [11]. ART-838 is a second-generation artemisinin derivative, which includes dimers and trimers of the named drugs. The dimers and trimers were developed to increase stability, bioavailability, half-life, and efficacy. Trioxane dimers are one subset of semi-synthetic dimeric artemisinin derivatives, characterized by two artemisinin monomers coupled by a linker of varying length, flexibility, and composition, with enhanced antimalarial, antimicrobial, and antineoplastic activity over first-generation artemisinins [13-24]. ART-838 (artemisinin-derived trioxane diphenylphosphate dimer 838) exhibits enhanced antineoplastic activity over the artemisinin monomer or the monomeric artemisinin derivative, AS [22,25]. Other phosphate ester derivatives of artemisinin have demonstrated enhanced anti-leukemic activity [26].

The artemisinins that may be used in the methods of the present invention include, but are not limited to, each of the artemisinin disclosed herein and they include artesunate (AS), dihydroartemisinin (DHA; also termed "artenimol"), artemether, arteether, artelinate, ART-838, ART-762, ART-851, ART-836, ART-853, ART-855, ART-895, ART-907, ART-923 and others disclosed in [63]. When referring to "the artemisinin" or "an artemisinin", it should be understood that these terms refer to both a monomeric artemisinin as well as dimeric, trimeric or multimeric artemisinins.

Second Agents

As indicated above, the methods of the present invention are practiced using combinations of an artemisinin and a second agent. The second agent may be any drug, toxin, poison, agent, etc. that has the ability to inhibit, block, kill, etc. a cancer cell. Suitable second agents include several different classes of second agents, e.g., BCL-2 inhibitors, kinase inhibitors, inhibitors of other enzymes and pathways involving activities crucial to cancer, and anti-neoplastic agents including biological molecules as well as small molecule drugs.

The BCL-2 inhibitors include, but are not limited to, ABT-199, ABT-263, and ABT-737.

The kinase inhibitors include, but are not limited to, lestaurtinib (LES), midostaurin (MID), and sorafenib (SOR), all of which target multiple kinases, including FLT3.

The anti-neoplastic agents include, but are not limited to, cytarabine (ARA), doxorubicin (DOX) [29,57], etoposide (ETO), cyclophosphamide [58], triplotide [59], vinorelbine, cisplatin [38], and rituximab [60].

When referring to "the second agent" or "a second agent", it should be understood that these terms refer to both a single second agent as well as two or more second agents.

Combinations

As summarized above, there are a number of different combinations of an artemisinin and a second agent may be used when practicing the various embodiments and aspects of the invention. Such combinations include, but are not limited to, those where the artemisinin is AS and the second agent is one or more agents selected from among ABT-737, ABT-199, ARA, DOX, ETO, MID, LES, and SOR. Additional combinations include, but are not limited to, those where the artemisinin is ART-838 and the second agent is one or more agents selected from among ABT-737, ABT-199, ARA, DOX, ETO, MID, LES, and SOR.

Cancer

The methods of the present invention can be used in the treatment of a variety of cancers. It will be apparent that different combinations of the drugs can be used in the treatment of different types of cancer. It will also be apparent that particular combinations of drugs may differ in effectiveness depending on the type of cancer, the stage and grade of a particular cancer, the physical location of the cancer within the subject, the molecular abnormalities in the cancer, and available means for administering the drugs, among other factors.

Exemplary cancers that may be treated via the methods of the invention include, but are not limited to, leukemias including acute leukemias, such as acute myeloid leukemia (AML) and acute lymphoid leukemia (ALL; including B cell ALL (B-ALL) and T cell ALL (T-ALL)), chronic leukemias, such as chronic myeloid leukemia (CML) and chronic lymphoid leukemia (CLL); lymphoma; myeloma; myelodysplastic syndrome; non-small cell lung cancer; pancreatic cancer; gastric cancer; Kaposi's sarcoma; hepatocellular carcinoma; osteosarcoma; laryngeal squamous cell carcinoma; metastatic uveal melanoma; lung and splenic metastases; advanced non-small cell lung cancer; cervical carcinoma; colorectal cancer; breast cancer; prostate cancer; and all other hematologic malignancies and solid cancers including brain cancer.

Pharmaceutical Compositions

The artemisinins and the second agents used in the methods of the invention may be formulated in pharmaceutical compositions comprising pharmaceutically acceptable carriers, excipients and/or diluents. It will be apparent that depending on the identity of the particular drugs being used in the combinations, a suitable pharmaceutical composition may comprise a single drug or type of drug (i.e., one or more artemisinin) or two or more drugs or types of drug (i.e., one or more artemisinin and one or more second agent).

The pharmaceutical compositions may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In preferred aspects of each of the embodiments on the invention, the pharmaceutical composition is administered to the subject as an oral formulation.

Pharmaceutically acceptable carriers, excipients and diluents are those compounds, solutions, substances or materials that can be used to produce formulations of the drugs that are suitable to be administered to a subject, such as a human. In particular, carriers, excipients and diluents of the present invention are those useful in preparing a pharmaceutical composition that is generally safe, non-toxic and neither biologically nor otherwise undesirable and that may present pharmacologically favorable profiles, and includes carriers and diluents that are acceptable for veterinary use as well as human pharmaceutical use. Suitable pharmaceutically acceptable carriers, excipients and diluents are well known in art and can be determined by those of skill in the art as the clinical situation warrants. Examples of suitable carriers and diluents include dextrose, water, glycerol, ethanol, propylene glycol, polysorbate 80 (Tween-80™), poly (ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin), hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. More particularly: (1) 5% (w/v) dextrose, or (2) water (e.g., sterile water; Water-For-Injection), may be used as a pharmaceutically acceptable carrier. Pharmaceutically acceptable diluents also include tonicity agents that make the composition compatible with blood. Tonicity agents are particularly desirable in injectable formulations.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavoring agents, coloring agents, administration aids, and combinations thereof.

The pharmaceutical compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Acceptable methods for preparing the pharmaceutical compositions according to the invention are known to those skilled in the art. For example, pharmaceutical compositions may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

Modes of Administration

The pharmaceutical compositions and the drugs of the present invention may be formulated, for example, for oral, enteral, sublingual, intranasal, intraocular, rectal, intravaginal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In certain aspects of each of the embodiments of the invention, the pharmaceutical compositions are administered to the subject intravenously.

Formulations for parenteral administration can be in the form of aqueous or non-aqueous isotonic sterile solutions, suspensions or fat emulsions. The unit dosage of these solutions or suspensions can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants. In an alternative embodiment, the parenteral unit dosage form of pharmaceutical compositions and the antibacterial agents of the present invention can be a ready-to-use solution of the pharmaceutical compositions and the antibacterial agents in a suitable carrier in sterile, hermetically sealed ampoules or in sterile pre-loaded syringes. The suitable carrier optionally comprises any of the above-mentioned excipients. The parenteral form used for injection must be fluid to the extent that easy syringability exists.

Excipients used in parenteral preparations may also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vasoconstrictors for prolongation and agents that increase tissue permeability), and combinations thereof.

Parenteral formulations using hydrophobic carriers include, for example, fat emulsions and formulations containing lipids, liposheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include 5% dextrose in water.

In intramuscular preparations, a sterile formulation of the pharmaceutical compositions of the present invention can be dissolved and administered in a pharmaceutical diluent such as Water-for-Injection (WFI) or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

When formulated into separate pharmaceutical compositions, the pharmaceutical compositions may be administered via the same or different modes of administration. In certain aspects of each invention, the artemisinin and the second agent are administered to the subject in the same pharmaceutical composition and via the same mode of administration.

The timing of administration used in the methods of the invention will vary depending on a number of factors, including whether there is concurrent or sequential administration, the identity of the drugs, the identity of the cancer, the physical characteristics of the subject, the severity of the subject's symptoms, and the formulation and the means used to administer the drugs, among other factors. However, administration frequencies of the drugs will generally include 4, 3, 2 or once daily, every other day, every third day, every fourth day, every fifth day, every sixth day, once weekly, every eight days, every nine days, every ten days, bi-weekly, monthly and bi-monthly, whether the drugs are administered alone or in combination, concurrently or sequentially. In certain aspects, the concurrent or sequential administration is administration once daily. The duration of treatment will be based on the cancer being treated and will be best determined by the attending physician. Under some conditions, treatment will be continued for a number of days, weeks, or months. Under other conditions, complete treatment will be achieve through administering one, two or three doses of the combinations over the entire course of treatment.

Methods of Treatment

As discussed in the summary of the invention above, methods of the invention include methods of treating cancer in a subject comprising administering therapeutically effective amounts of an artemisinin and a second agent to a subject having cancer. The artemisinin and the second agent may be administered in either order, sequentially or concurrently, with overlapping or non-overlapping periods of administration. The methods of the invention thus include methods of treating cancer in a subject, comprising concurrently administering therapeutically effective amounts of an artemisinin and a second agent to a subject having cancer. The methods of the invention thus also include methods of treating cancer in a subject, comprising sequentially administering therapeutically effective amounts of an artemisinin and a second agent to a subject having cancer.

The terms "treating" and "treatment" mean at least the mitigation of cancer, or a disease condition or symptom associated with cancer in a subject that is achieved by a reduction of growth, replication, and/or propagation, or death or destruction of cancer and/or cancer cells, on or in the subject. The terms "treating" and "treatment" include curing, healing, inhibiting, relieving from, improving and/or alleviating, in whole or in part, the cancer or associated disease condition or symptom. The mitigation of cancer or associated disease condition or symptom may be about 100%, 99%, 98%, 97%, 96%, 95%, 90%, 80%, 70%, 60%, 50%, 40%, 30%, 20%, 10%, 5% or 1% in the subject, versus a subject to which the combinations taught herein have not been administered. In one aspect, treating means reducing the population of cancer cells causing the cancer in the subject to an undetectable level, where detection is by any conventional means, such assay a blood sample in the laboratory. In another aspect, treating means complete healing of the cancer, shown by an absence of clinical symptoms associated with the cancer. In a further aspect of the invention, treating means the mitigation of cancer or an associated disease condition or symptom by at least about 90% in the subject. In an additional aspect, treating means the mitigation of cancer or an associated disease condition or symptom by at least about 95% in the subject.

The amount of the drugs sufficient to have an additive or synergistic effect on cancer in a subject will vary, for example, in view of the identity of the drugs being used in the combination, the physical characteristics of the subject, the severity of the subject's symptoms, the form of the cancer, the identity of the cancer, the formulations and means used to administer the drugs, and the method being practiced. The specific dose for a given subject is usually set by the judgment of the attending physician. However, in each dose comprising an artemisinin is typically between about 0.1 and about 100 mg/kg body weight. In some aspects, about 0.5-50 mg/kg, about 0.5-40 mg/kg, about 0.5-30 mg/kg, about 0.5-20 mg/kg, about 1-20 mg/kg, about 2-20 mg/kg, about 2-10 mg/kg, about 2-8 mg/kg, about 2-6 mg/kg, about 5-100 mg/kg, or about 10-100 mg/kg body weight.

In each dose comprising a BCL-2 inhibitor, the amount of the drug is typically between about 0.1 and about 50 mg/kg body weight. In some aspects, about 0.1-40 mg/kg, about 0.1-30 mg/kg, about 0.1-20 mg/kg, about 0.1-25 mg/kg, about 0.1-10 mg/kg, about 1-50 mg/kg, about 2-50 mg/kg, about 2.5-50 mg/kg, about 2.5-40 mg/kg, about 2.5-30 mg/kg, or about 2.5-20 mg/kg body weight.

In each dose comprising a kinase inhibitor, the amount of the drug will vary due to the size of this class of agents. However, it will typically be between about 0.1 and about 100 mg/kg body weight.

In each dose comprising an anti-neoplastic agent, the amount of the drug will vary due to the size of this class of agents. However, it will typically be between about 0.1 and about 100 mg/kg body weight.

Depending on the means of administration, the dose may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours. The administration of the dose may be interrupted, such as where the dose is administered via intravenous infusion and the dose is divided into two or more infusion bags. Under such circumstances, the administration of the dose may be interrupted while the infusion bags are changed.

As used herein, the terms "dose", "unit dose", "dosage", "effective dose" and related terms refer to physically discrete units that contain a predetermined quantity of active ingredient (drug) calculated to produce a desired therapeutic effect. A single dose is thus a predetermined quantity of an artemisinin and/or second agent that is administered to a subject.

As used herein, a "subject" is a human, a non-human primate, bird, horse, cow, goat, sheep, a companion animal, such as a dog, cat or rodent, or other mammal.

Additive and Synergistic Effects

In many instances, the combinations of drugs taught herein, i.e., the combinations of artemisinins and second agents, target two different aspects of a cancer cell, such as two different structures, or two different pathways, or a structure on one hand and a pathway on the other. As a result, while the combinations of artemisinins and second agents may have an additive therapeutic effect on a cancer, the combinations may also have a synergistic therapeutic effect on the cancer. Synergistic therapeutic effects are those that are substantially greater than what is seen when cancer cells are treated with either drug alone.

In a particular aspect, the invention is directed to a method of treating cancer in a subject, comprising concurrently administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have an additive therapeutic effect on the cancer.

In a particular aspect, the invention is directed to a method of treating cancer in a subject, comprising concurrently administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have a synergistic therapeutic effect on the cancer.

In a particular aspect, the invention is directed to a method of treating cancer in a subject, comprising sequentially administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have an additive therapeutic effect on the cancer.

In a particular aspect, the invention is directed to a method of treating cancer in a subject, comprising sequentially administering therapeutically effective amounts of an artemisinin and a second agent to a subject having cancer, wherein the artemisinin is AS or ART-838, wherein the second agent is ABT-737, ABT-199, ARA, DOX, ETO, MID, LES or SOR, and wherein the combination of the artemisinin and the second agent have a synergistic therapeutic effect on the cancer.

III. Examples

Materials and Methods

Reagents

Synthesis of ART-838, its parent alcohol ART-606, deoxy-ART-838, and DHA were as described [9,22,25]. AS was from LKT Laboratories (St. Paul, Minn.); Etoposide (ETO), Cytarabine (ARA), Doxorubicin (DOX), Tiron, deferoxamine mesylate (DFO), NAC, phorbol 12-myristate 13-acetate (PMA), and actinomycin-D were from Sigma-Aldrich (St.

Louis, Mo.); Lestaurtinib (LES), Midostaurin (MID) z-VAD (OMe)-fmk (z-VAD), ABT-199, and ABT-737 were from Santa Cruz Biotechnology (Dallas, Tex.); Sorafenib (SOR) was from LC laboratories (Woburn, Mass.). ART-838, AS, ETO, LES, MID, SOR, z-VAD, ABT-199, ABT-737, PMA, and actinomycin-D were stored in DMSO (Mediatech, Manassas, Va.); ARA, Tiron, and DFO in sterile water; DOX in PBS. All drug stocks were stored at −20° C. NAC was dissolved in culture medium, pH adjusted to 7.4, and filtered immediately before use. Final DMSO concentrations were the same for all samples in any given experiment and always <0.8%. The kinase inhibitor library used for the drug combination screen was generously provided by Dr. Jeffrey Tyner (Oregon Health & Science University Knight Cancer Institute), and stored at −20° C. until 1 hour before use.

Cells

MOLM14 cells were provided by Dr. Feyruz Rassool (University of Maryland School of Medicine (UMSOM)). Ba/F3/WT-FLT3 and Ba/F3/ITD cells were provided by Dr. Maria Baer (UMSOM). All other cell lines were obtained from ATCC or DSMZ. Cell lines were cultured (37° C., 5% $CO_2$) in RPMI 1640 containing L-glutamine (Mediatech) and 10% FBS (Gemini Bio-products, West Sacramento, Calif.). Ba/F3/WT-FLT3 cells were also supplemented with 10 ng/ml recombinant murine IL-3 (Peprotech, Rocky Hill, N.J.).

Cytotoxicity

Cytotoxicity was assessed using alamarBlue assays (Life Technologies, Grand Island, N.Y.; used for $IC_{50}$ determinations and all drug combinations except the drug combination screen (method described separately below)) or Trypan Blue dye exclusion (Life Technologies, Grand Island, N.Y.; used only for experiments using inhibitors that could interfere with alamarBlue assay performance (NAC, Tiron, DFO)).

AlamarBlue Assays

Cell lines were seeded in 96-well tissue culture plates at $10^4$ cells per well (myeloid leukemia lines) or $2\times10^4$ cells per well (lymphoid leukemia lines) in culture medium, followed by addition of drugs at the indicated concentrations. 2-4 wells per plate containing media-only were included for background subtraction. Peripheral wells were filled with sterile water to minimize the effects of evaporation. Plates were incubated for ~48 hours at 37° C. with 5% $CO_2$, then 1/10 volume (10 µl according to the manufacturer's instructions. Fluorescence was measured using a VICTOR X3 multilabel plate reader (PerkinElmer, Waltham, Mass.). Background fluorescence was subtracted from fluorescence of all experimental wells. The effect of each drug concentration on viability was calculated as a percentage of the result for vehicle-treated cells. For AS and ART-838 $IC_{50}$ determinations, each cell line was tested in triplicate and in at least three independent experiments. $IC_{50}$ (concentration that inhibits growth by 50%) values were calculated using CompuSyn software (ComboSyn, Paramus, N.J.).

Trypan Blue Dye Exclusion Assays

Cells were pretreated with NAC (25 mM), Tiron (1 mM), or DFO (11 µM) for 60-120 minutes, and then treated with a range of concentrations of AS or ART-838 and incubated at 37° C. with 5% $CO_2$. Preliminary experiments showed that Tiron, NAC, and DFO were cytotoxic to MOLM14 cells at high concentrations, so each was used at its approximate 48-hour $IC_{50}$ (concentration that inhibited growth by only 50% by 48 hours). 48 hours after addition of the drugs, viable cell counts were obtained via Trypan Blue dye exclusion. The effect of each drug concentration on viability was calculated as the percentage of the result for vehicle-treated cells with or without inhibitor pretreatment and $IC_{50}$s were calculated as described above.

Apoptosis

Drug or vehicle-treated cells ($1-5\times10^5$/sample) were washed with cold PBS, resuspended in Annexin-V binding buffer, co-stained with 5 µl each of APC Annexin-V and 7-AAD viability dye (all from BioLegend, San Diego, Calif.), and incubated for 15 minutes at room temperature in the dark then stored on ice until analysis (<30 minutes). Stained cells were analyzed using the FL3 and FL4 channels of an Accuri C6 flow cytometer. ~10,000 non-debris cellular events were collected per sample and analyzed, as for cell cycle. The Annexin-$V^-$/7-$AAD^-$ population was designated "viable," the Annexin-$V^+$/7-$AAD^-$ population was designated "early apoptotic," and the Annexin-$V^+$/7-$AAD^+$ population was designated "dying/dead" [47].

ROS—Mitochondrial Superoxide

Cells were pretreated with NAC, Tiron, DFO, or vehicle then treated with AS, ART-838, or vehicle, as described above, then following a 16-hour drug treatment, cells were loaded with 5 µM MitoSOX Red (Invitrogen, Carlsbad, Calif.) for 30 minutes at 37° C. with 5% $CO_2$, then analyzed using the FL2 channel of an Accuri C6 flow cytometer.

Drug Combination Analysis (Using the Methods of Chou and Talalay)

Combinations of AS or ART-838 with cytarabine, doxorubicin, etoposide, doxorubicin, etoposide, lestaurtinib, midostaurin, or sorafenib AS and ART-838 were each tested in combination with cytarabine (ARA), doxorubicin (DOX), etoposide (ETO), lestaurtinib (LES), midostaurin (MID), or sorafenib (SOR), using simultaneous treatment of MOLM14 or KOPN8 cells for 48 h. For each two-drug pair, dose-response curves were generated for each drug individually and for the two drugs combined. Stocks of each drug were prepared at 67.5× (MOLM14) or 45×(KOPN8) the approximate 48 h $IC_{50}$ and combined in equal parts with the other drug or vehicle. Six (MOLM14) or five (KOPN8) 1.5-fold serial dilutions were prepared for each drug or combination, and each dilution was added to wells of cells in triplicate at 1/10 final well volume, to achieve final concentrations of $3.375\times IC_{50}$ (MOLM14 only), $2.25\times IC_{50}$, $1.5\times IC_{50}$, $1\times IC_{50}$, $0.67\times IC_{50}$, and $0.44\times IC_{50}$, as determined in pilot experiments to achieve a wide effect range. This design is based on the recommendation of Chou that combination experiments be performed with drugs combined in an equipotent ratio based on their respective single-drug $IC_{50}$ values [48]. Following a 48-hour incubation with each drug or drug pair, cytotoxicity assays were performed using alamarBlue as described above.

For combination experiments in which the sequence of treatment with 2 drugs varied, MOLM14 cells were plated at the same time and treated in 3 sequences (depicted at the bottom of FIG. 5): (1) SOR before AS or ART-838—cells were treated with SOR for 24 hours then AS or ART-838 was added for an additional 48 hours, (2) AS or ART-838 and SOR simultaneously—cells were treated with vehicle only for 24 hours then SOR and AS or ART-838 were added for an additional 48 hours, and (3) AS or ART-838 before SOR—cells were treated with AS or ART-838 for 24 hours then SOR was added for an additional 48 hours. Combination index (CI) values were generated by median-effect analysis, using CompuSyn software, based on the median-effect principle of the mass action law and the combination index theorem of Chou and Talalay, wherein CI values <1 are defined as synergistic, CI values ~1 as additive, and CI values >1 as antagonistic [48-50]. Each set of drug combinations was tested in at least three independent experiments, each in triplicate.

Combinations of AS or ART-838 or DHA with ABT-199 or ABT-263 or ABT-737

MOLM14 or KOPN8 cells were seeded in 96-well plates as described above for alamarBlue assays. Cells were treated with a certain concentrations of AS, or ART-838 or DHA, in combination with a range of concentrations of ABT-199 or ABT-263 or ABT-737. AlamarBlue assays were performed as described above. Each set of drugs or drug combinations was tested in triplicate. Chou-Talalay drug combination analysis was performed as above.

Kinase Inhibitor Drug Combination Screen

The library used for screening contained 122 different drugs (mostly small-molecule kinase inhibitors), 19 of which were duplicated. Plates (3×384-well per set) contained 7 graded concentrations of each drug at 2× final concentration in culture media in 25 µl/well. Cells were mixed with AS or ART-838 at 2× the approximate $IC_{50}$, or vehicle (0.035% DMSO), in culture media and immediately added to drug plates at 25 µl/well using the Biomek FX automated liquid handling workstation (Beckman Coulter, Brea, Calif.), diluting AS and ART-838, as well as the drug library to their final 1× concentrations. Cells were plated such that each well contained 2500 cells (MOLM14 and Kasumi-1) or 5000 cells (KOPN8 and RCH-ACV). Cells were incubated for 48 hours (37° C., 5% $CO_2$) then 10 µl MTS solution (Promega, Madison, Wis.) was added per well using the Biomek FX automated liquid handling workstation. Plates were incubated for 2-3 hours (37° C., 5% $CO_2$) then absorbance was read at 490 nM using a PHERAstar FS multimode microplate reader (BMG LABTECH, Ortenberg, Germany). Each plate contained two positive control wells used for background subtraction. Each plate also contained 45 wells without any drug. The background-subtracted absorbance for each well was normalized to the average of the no-drug wells from the corresponding vehicle plate. The average of the no-drug wells for each AS or ART-838-containing plate were used to determine the effects of AS or ART-838 alone.

Bliss-Independence Analysis of Drug Interactions

AS/ART-838/kinase inhibitor library drug combination screen data were analyzed by comparing the observed cytotoxicity of each combination to the additive effect predicted by the Bliss-independence model (calculated by the formula: [Effect of Drug 1+Effect of Drug 2]−[Effect of Drug 1× Effect of Drug 2]) [43,51]. Hits were ranked by the observed inhibition over the Bliss independence prediction.

Combinatorial Effect of ARA with ART-838 in Delaying Subcutaneous Luciferase Labeled MOLM14 (MOLM14-Luc) Xenograft Growth in NSG Mice Highly immunodeficient NSG mice, obtained originally from Jackson Laboratory (Bar Harbor, Me.), were bred and housed in the UMSOM animal facilities, and handled in a laminar flow hood under aseptic conditions. All experiment procedures and animal care were in compliance with the NIH guidelines for the Care and Use of Laboratory Animals and approved by the UMSOM Institutional Animal Care and Use Committee. ART-838 were formulated in Tween 80:ethanol (7:3, v:v) and diluted 1:10 in filtered deionized water immediately before administration. For the human AML xenograft model, 6-12-week-old male NSG mice (>20 g) were transplanted sc with MOLM14-luc cells on day 0 and drug-treated via oral gavage, as specified in legend. Mice were monitored daily and euthanized when tumors reached an estimated mass of 2000 mg (using the formula: [length×width2]/2, assuming density=1 mg/mm3) [64].

Combinatory Effect of SOR with AS in Delaying Subcutaneous MOLM14 Xenograft Growth in NSG Mice The NSG mice were obtained, maintained and handled as described in the paragraph immediately above. AS was also formulated in Tween 80:ethanol (7:3, v:v) and diluted 1:10 in filtered deionized water immediately before administration. For the human AML xenograft model, 6-12-week-old male NSG mice (>20 g) were transplanted sc with MOLM14 cells on day 0 and drug-treated via oral gavage, as specified in legend. Mice were monitored daily and euthanized when tumors reached an estimated mass of 2000 mg as described in the paragraph immediately above [64].

Statistics

Differences between groups were compared using the Student's t test. Prism (Graphpad, La Jolla, Calif.) software was used for correlation analyses.

Results #1

ART-838 Enhanced Cytotoxicity of Other Anti-Leukemic Agents

Figure 2A:
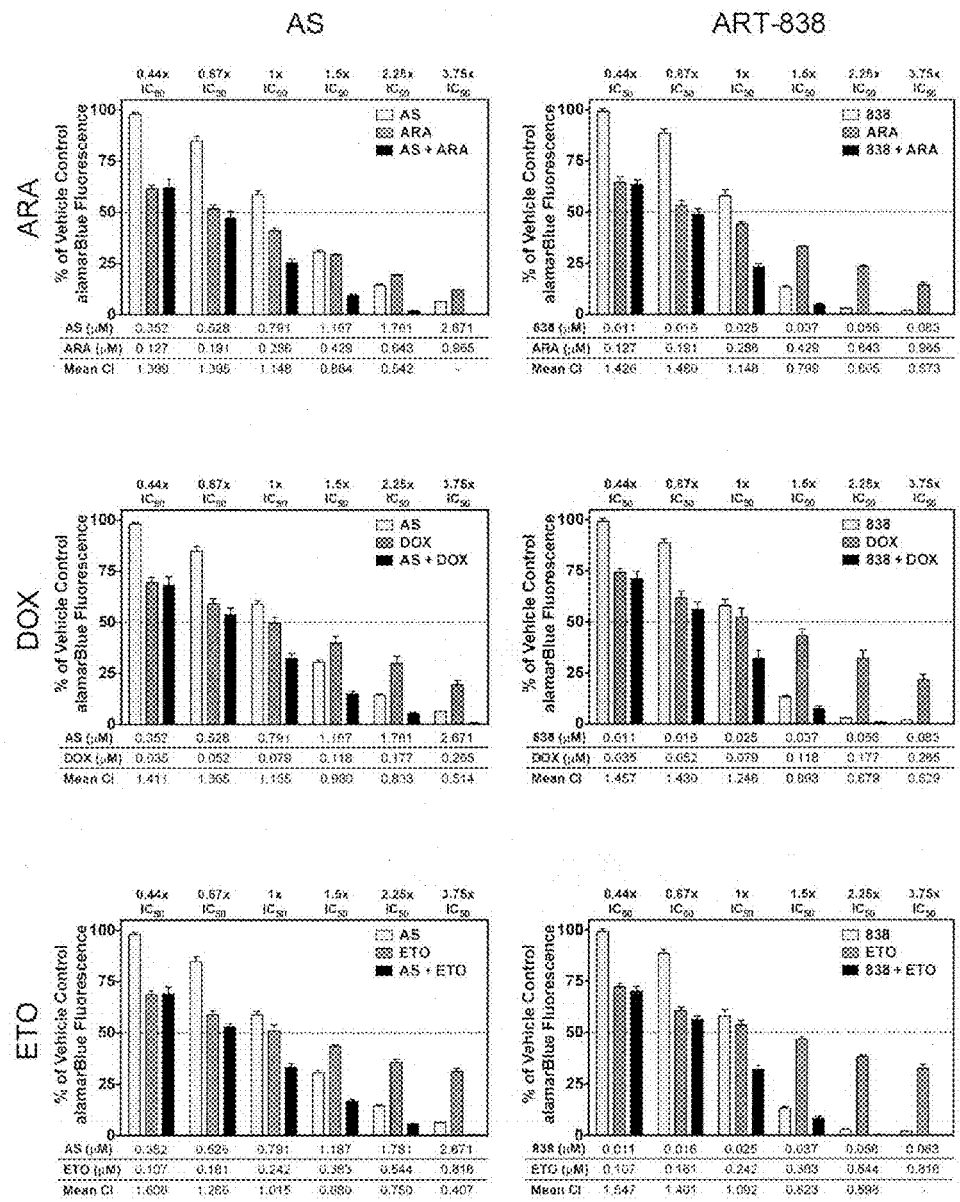
FIGS. 2A-2B. ART-838 or AS enhanced the cytotoxicity of all six antileukemic drugs tested in MOLM14. MOLM14 cells were treated for 48 h with a range of concentrations of ART-838 or AS, alone or in combination with a range of concentrations of (FIG. 2A) standard antileukemic drugs (ARA, DOX, or ETO), or (FIG. 2B) kinase inhibitors (LES, MID, or SOR) at a ratio of the $IC_{50}$s for each drug for 48 h (Table 1), and cytotoxicity was assayed using alamarBlue. Each experiment was performed three times in triplicate, and error bars represent the SEM. All panels have error bars but some are too small to be visible. Combination indices (CI) were computed for each drug combination using CompuSyn software, based on the Median Effect Principle and the CI theorem of Chou-Talalay, wherein CI=1 indicates additivity, CI<1 synergism, and CI>1 antagonism.
Figure 2B:
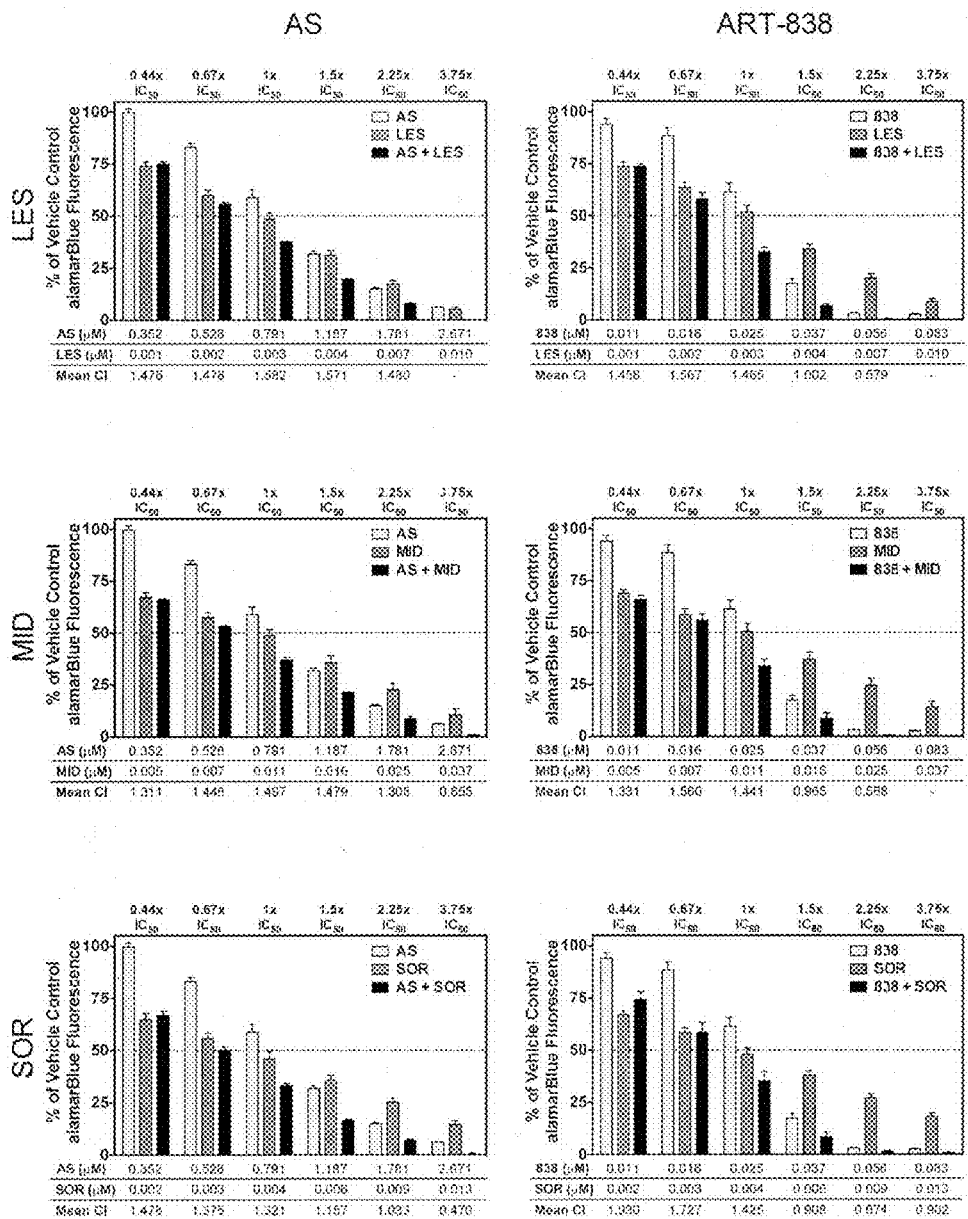
Figure 3B:
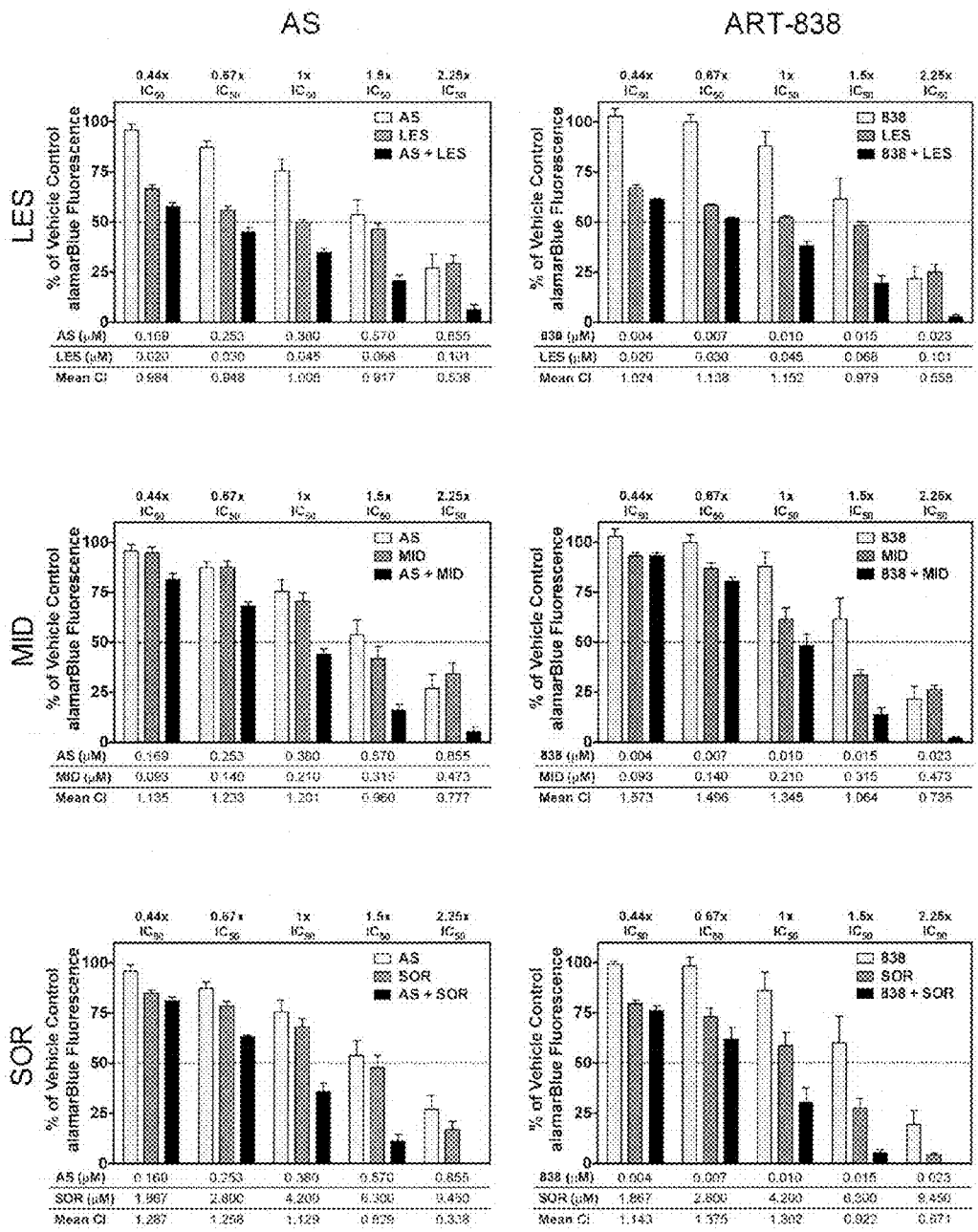

Drug combinations were investigated by testing the interactions of ART-838 or AS with three standard anti-leukemic drugs (ARA, DOX, ETO) and three kinase inhibitors (MID, LES, SOR; all of which target multiple kinases, including FLT3) [4]. MOLM14 cells were treated with each of these drugs, alone and in combination with ART-838 or AS at an equipotency ratio based on the $IC_{50}$s for each drug (Table 1) [50]. In Table 1, KOPN8 and MOLM14 cell lines were treated with a range of concentrations of each drug for 48 h then cytotoxicity was measured via alamarBlue assay. Results were normalized to cells treated with vehicle (≤0.5% DMSO) alone. $IC_{50}$s were calculated using CompuSyn software and represent the means of at least three experiments performed in triplicate. Addition of ART-838 or AS enhanced the cytotoxicity of all six tested drugs across a range of concentrations (FIG. 2). Drug interactions were typically most favorable (more additive/synergistic or less antagonistic) at higher doses. Similar results were seen in KOPN8 cells (FIG. 3).

TABLE 1

| Cell Line | ARA $IC_{50}$, µM | DOX $IC_{50}$, µM | ETO $IC_{50}$, µM | MID $IC_{50}$, µM | LES $IC_{50}$, µM | SOR $IC_{50}$, µM |
|---|---|---|---|---|---|---|
| KOPN8 | 0.073 | 0.030 | 0.150 | 0.210 | 0.045 | 4.20 |
| MOLM14 | 0.286 | 0.079 | 0.242 | 0.011 | 0.003 | 0.004 |

Figures 4A, 4B, 4C, 4D:
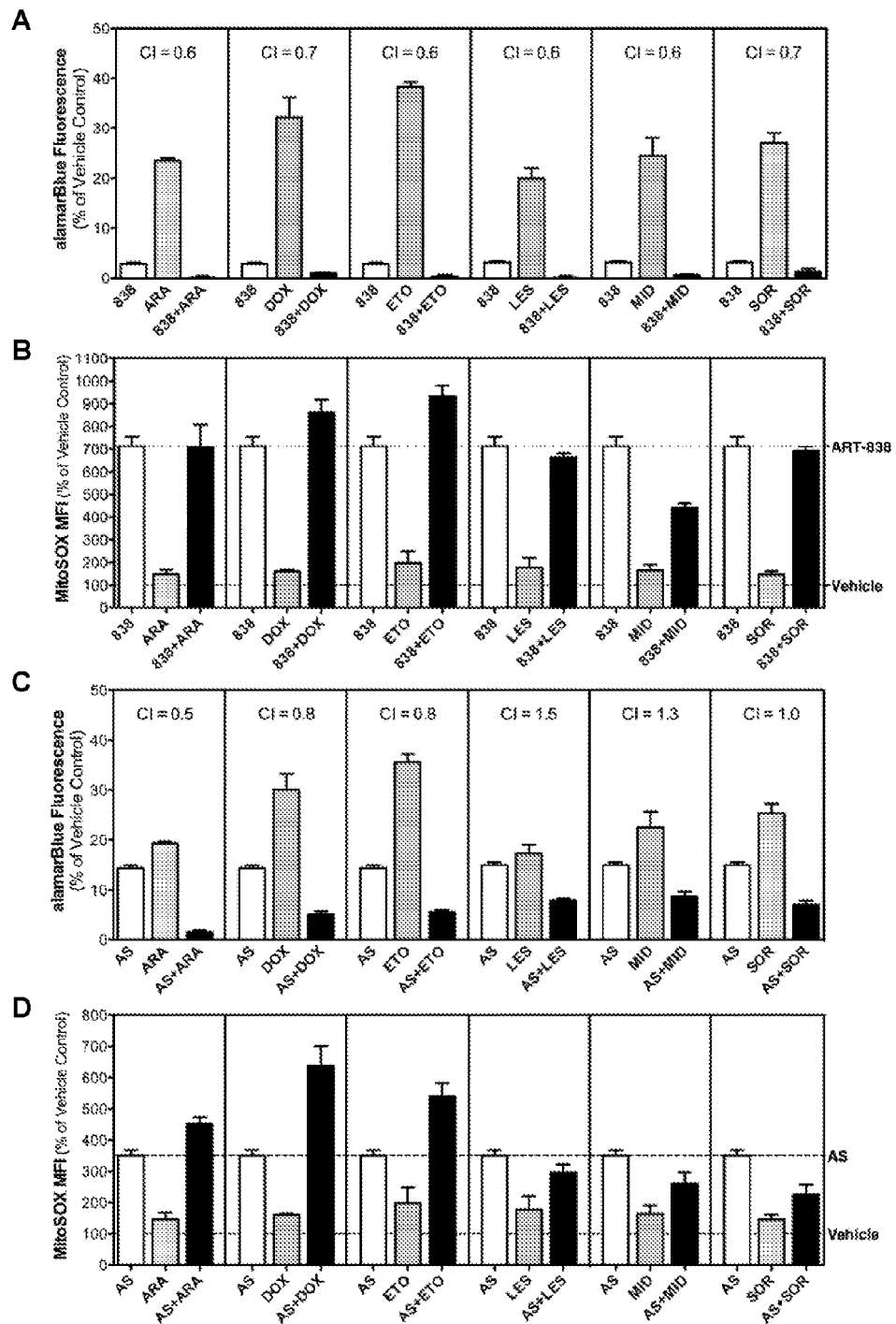
FIGS. 4A-4D. Effects of ART-838- and AS-containing drug combinations on MOLM14 growth and superoxide generation.

Combinations of each drug with ART-838 or AS at 2.25× their respective single-drug $IC_{50}$s in MOLM14 are highlighted in FIG. 4. Interactions between ART-838 and each of the six tested drugs were synergistic at these concentrations (CIs=0.6-0.7) (FIG. 4A), as were interactions between AS and each of the three standard antileukemic drugs (FIG. 4C). However, interactions between AS and SOR were only additive (CI=1.0), and interactions between AS and LES (CI=1.5) or MID (CI=1.3) were mildly antagonistic.

As both ART-838 and AS increased mitochondrial superoxide, and many antineoplastic drugs induce ROS generation [52,53], mitochondrial superoxide levels of MOLM14 cells treated with each of the above six antileukemic drugs were evaluated, alone and in combination with ART-838 or AS. All six drugs induced mitochondrial superoxide, although to a much lesser extent than did ART-838 (FIG. 4B) or AS (FIG. 4D). ARA, DOX, or ETO further enhanced AS-induced superoxide generation, while the kinase inhibitors LES, MID, and SOR reduced AS-induced superoxide. ART-838 alone induced superoxide to greater levels than AS. Only DOX and ETO further enhanced ART-838-induced superoxide generation. The differential interactions of ART-838 and AS with these kinase inhibitors suggests the possibility that ART-838 may have additional mechanisms of action beyond those of AS.

Figure 5:
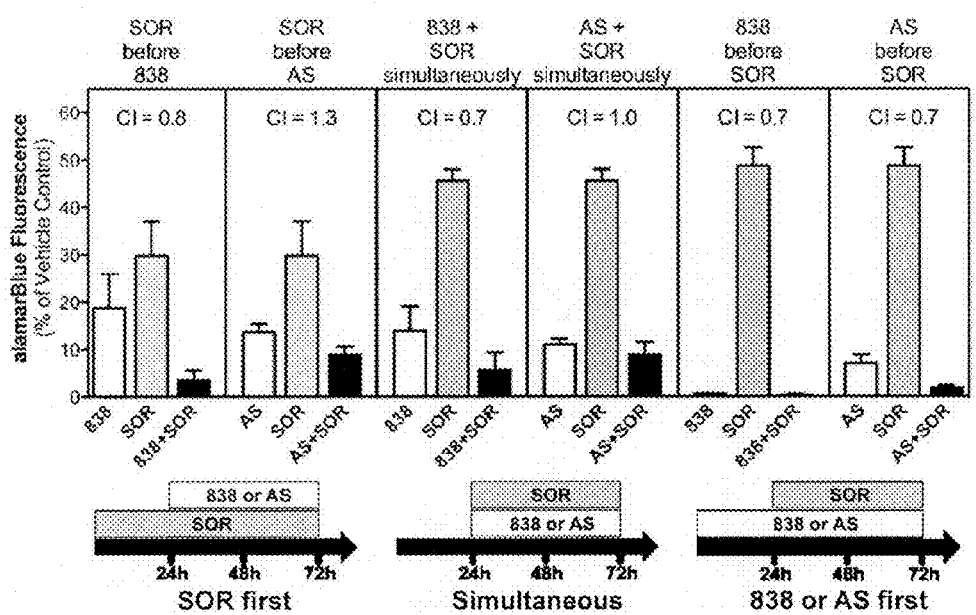
FIG. 5. Effects of sequence of administration on synergy between ART-838 or AS and SOR. MOLM14 cells were treated with SOR, ART-838, and/or AS, alone and in combination at the doses and ratios described in FIG. 2 in the sequences depicted at the bottom of the figure. After 72 h, cytotoxicity was assessed using alamarBlue. Full concentration-response curves are shown in FIG. 6. Shown here are the effects of each drug alone or in combination at 2.25× the approximate single-drug 48 h $IC_{50}$s. Error bars represent the SEM of three independent experiments, each in triplicate. CIs were computed as described above. All panels have error bars but some may be too small to be visible.
Figure 6A:
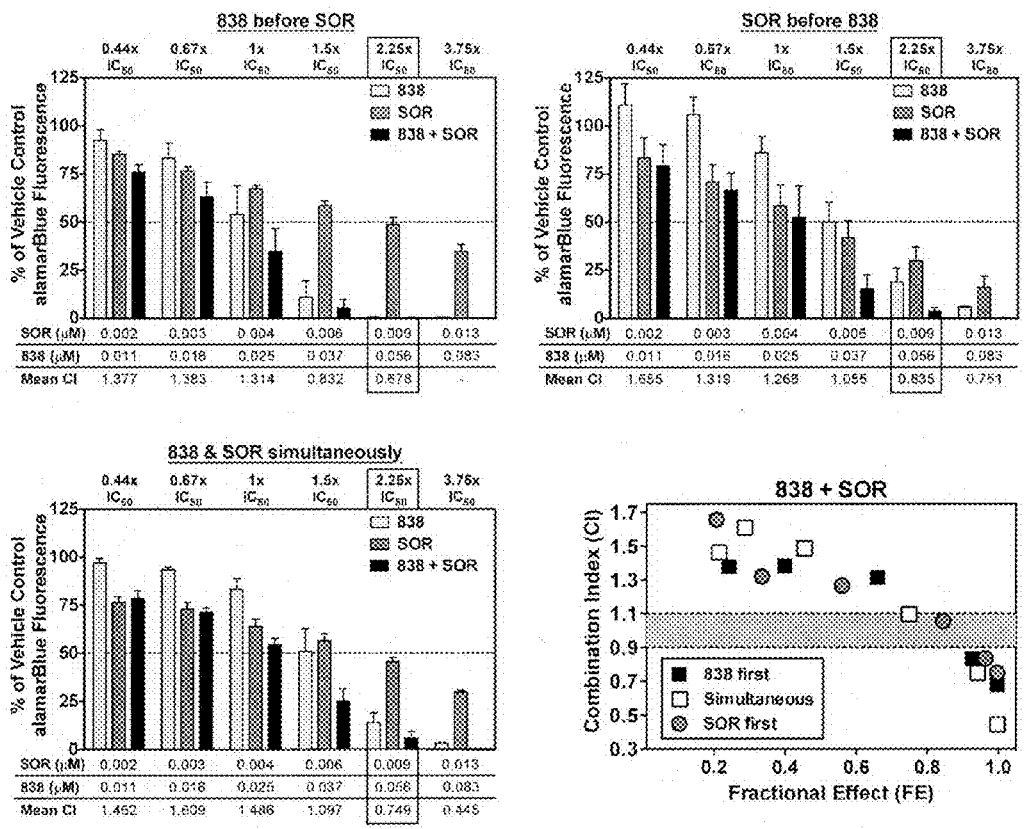
Figure 7A:
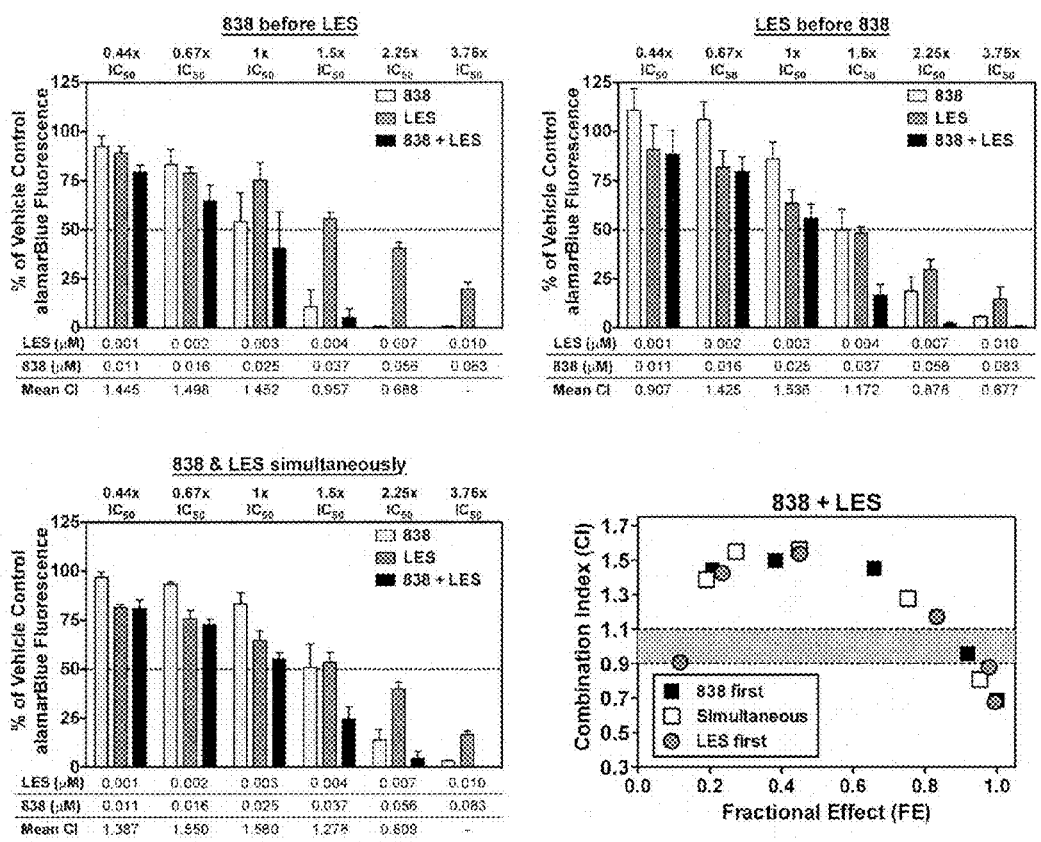

Synergy Between AS and SOR or LES was Dependent on Sequence of Administration while Synergy Between ART-838 and SOR or LES was Sequence-Independent Sequence of administration has been shown to be critical to optimizing synergy between FLT3 inhibitors and antineoplastic drugs in acute leukemia cells harboring mixed lineage leukemia gene rearrangements (MLLr) and/or FLT3 internal tandem duplication (FLT3/ITD) mutations [3,5,54], so the sequence-dependence of ART-838 or AS plus SOR or LES was assessed in MOLM14 cells. Sequences are depicted at the bottom of FIG. 5. Full concentration-response curves were obtained for each drug alone and in each combination/sequence (FIG. 6); combinations of SOR with ART-838 or AS at 2.25× their respective 48 h single-drug $IC_{50}$s are highlighted in FIG. 5. At these concentrations, simultaneous treatment with AS plus SOR caused additive cytotoxicity (CI=1.0); treatment with SOR before AS caused mild antagonism (CI=1.3); treatment with AS before SOR resulted in synergy (CI=0.7). In contrast, all 3 sequences of ART-838 combined with SOR resulted in synergistic growth inhibition (CIs=0.7-0.8). Similar results were seen with ART-838 or AS plus LES (FIG. 7). This difference in drug interactions is consistent with the possibility of mechanistic differences for ART-838 vs AS.

Discussion #1

One potential mechanism of synergy between artemisinins and other antineoplastic drugs is enhanced generation of ROS and induction of oxidative stress. Three drugs (ARA, DOX, and ETO) currently used to treat acute leukemias and known to generate ROS [52,53] were tested in combination with ART-838 or AS. ART-838 or AS enhanced the cytotoxic effects of each of these drugs. When ART-838 or AS and these standard antileukemic drugs were used at concentrations that caused ≥50% growth inhibition individually, their interactions were additive to synergistic. This might reflect a threshold effect wherein ROS levels must be raised beyond the cells' enhanced antioxidant capacity in order to achieve maximal cytotoxicity. ART-838, AS, ARA, DOX, or ETO each induced mitochondrial superoxide generation, and combination of ART-838 or AS with either DOX or ETO enhanced superoxide generation.

Since the most ART-838/AS-sensitive cell lines tested harbor FLT3/ITD and/or MLLr mutations—both known to elevate FLT3 signaling—3 kinase inhibitors known to target FLT3 (MID, LES, and SOR) were tested, in combination with ART-838 or AS. It was previously demonstrated that FLT3 inhibitors can reduce ROS levels in leukemia cells [55], which could reduce the efficacy of a drug that requires ROS generation for cytotoxicity, such as AS. A reduction in basal mitochondrial superoxide levels in response to these kinase inhibitors was not observed, but all three kinase inhibitors reduced AS-induced superoxide and MID reduced ART-838-induced superoxide.

In both MLLr ALL cells and FLT3/ITD+ AML cells, sequence of drug exposure is critical to optimizing synergy for FLT3 inhibitor-containing drug pairs [3,5,54]. It has been proposed that the strong synergy observed when leukemia cells are treated with standard chemotherapy followed by a FLT3 inhibitor is due to induction of DNA damage and pro-apoptotic signals by the standard antileukemic drugs followed by withdrawal of pro-survival/anti-apoptotic signals by FLT3 inhibition [3,5]. Three sequences of exposure to SOR or LES plus ART-838 or AS were tested. For AS-containing combinations, pretreatment with AS followed by addition of SOR (or LES) produced the greatest synergy. Simultaneous exposure was slightly less effective, and pretreatment with SOR (or LES) followed by addition of AS caused mild antagonism, perhaps due to reduced AS-induced superoxide in the presence of SOR. In contrast, sequence of administration had little effect on interactions between ART-838 and SOR, perhaps because ROS generation is not the only cytotoxic mechanism of ART-838. Differential interactions of ART-838 vs AS with kinase inhibitors were also recently reported for anti-cytomegalovirus activity [56]. These differences in drug interactions may aid in elucidating novel mechanisms of action of different artemisinin derivatives.

Results #2

Combinatorial Drug Screening Identified Synergistic Antileukemic Combinations with Artemisinins To identify (1) novel artemisinin-containing antileukemic drug combinations and (2) pathways that may compensate for those inhibited by artemisinins, a synthetic lethal drug combination screen was performed. AS or ART-838 was combined with a library of 122 different drugs (mostly small-molecule kinase inhibitors), 19 of which were duplicated, at seven graded concentrations, in four leukemia cell lines with different genetic backgrounds. MOLM14 is an AML cell line with an internal tandem duplication mutation in the FLT3 tyrosine kinase (FLT3/ITD) as well as a t(9; 11) chromosomal translocation, producing the MLL-AF9 fusion protein. Kasumi-1 is an AML cell line with a t(8; 21) translocation, producing a RUNX1-RUNX1T1 fusion, formerly known as AML1-ETO. KOPN8 is a B-ALL cell line with a t(11; 19) translocation producing the MLL-ENL fusion. Finally, RCH-ACV is a B-ALL cell line with a t(1; 19) translocation producing the E2A-PBX1 fusion. Cells were co-treated with AS or ART-838 at the approximate $IC_{50}$ (or vehicle) and the drug library for 48 h then cytotoxicity of the drugs was measured, singularly and in combination, via MTS assay.

Data were analyzed by comparing the observed cytotoxic effect of each drug combination with the predicted additive effect of that combination based on the Bliss-independence model (calculated by the formula: [Effect of Drug 1+Effect of Drug 2]−[Effect of Drug 1×Effect of Drug 2]) [43,51]. Combinations were ranked based on the average of the observed inhibition over the Bliss prediction for the seven concentrations of each kinase inhibitor. Combinations with positive values for this Bliss difference were considered synergistic, values near zero, additive, and negative values, antagonistic.

Figure 8:
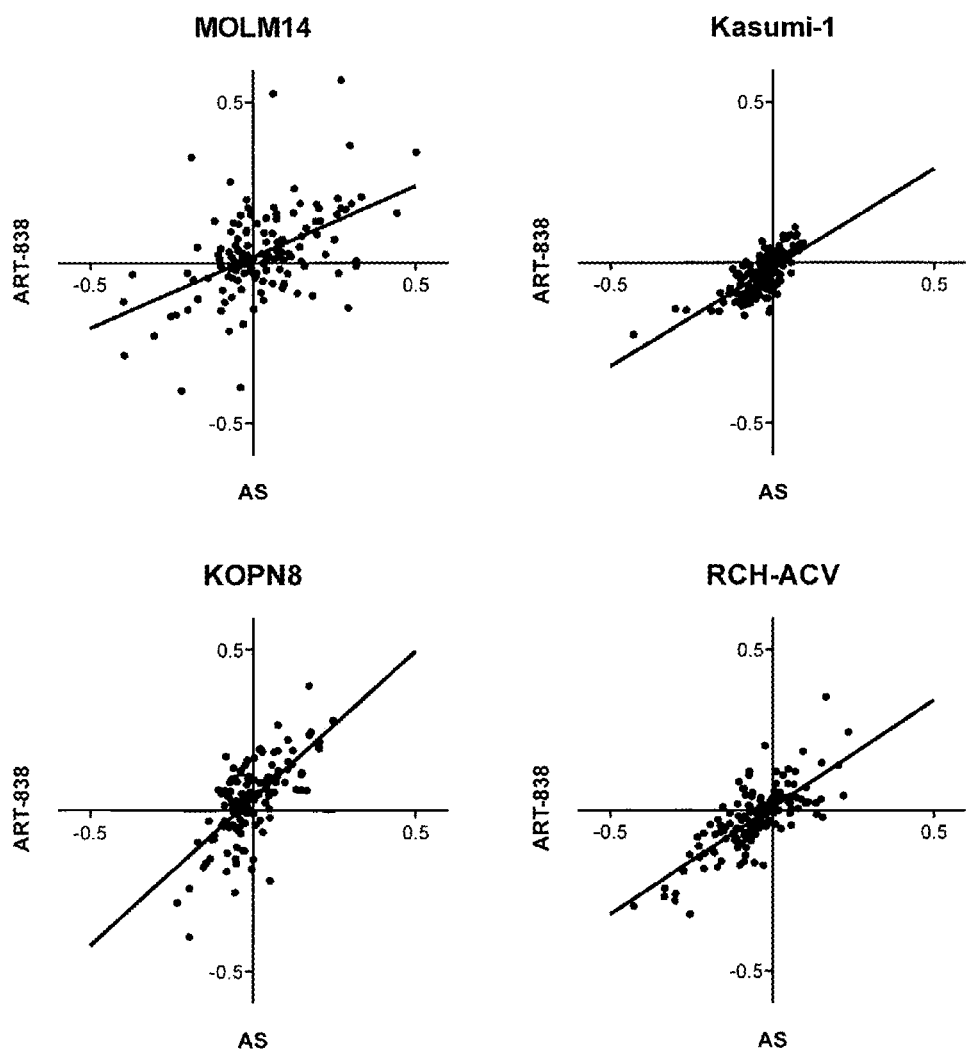
FIG. 8. Correlations between AS and ART-838 hits in four cell lines. A synthetic lethal drug combination screen was conducted. AS or ART-838 was combined with a library of 122 different drugs (mostly small-molecule kinase inhibitors). Cells were co-treated with AS or ART-838 at the approximate $IC_{50}$ (or vehicle) and the drug library for 48 h then cytotoxicity of the drugs was measured, singularly and in combination, via MTS assay. Spearman correlation coefficients (r) were calculated for the inhibition over Bliss prediction for each drug combination (n=141) with AS vs ART-838: MOLM14 r=0.44, Kasumi-1 r=0.66, KOPN8 r=0.64, RCH-ACV r=0.71. The data show highly significant positive correlations (P<0.001) between each drug combination with AS vs. ART-838.
Figure 9B:
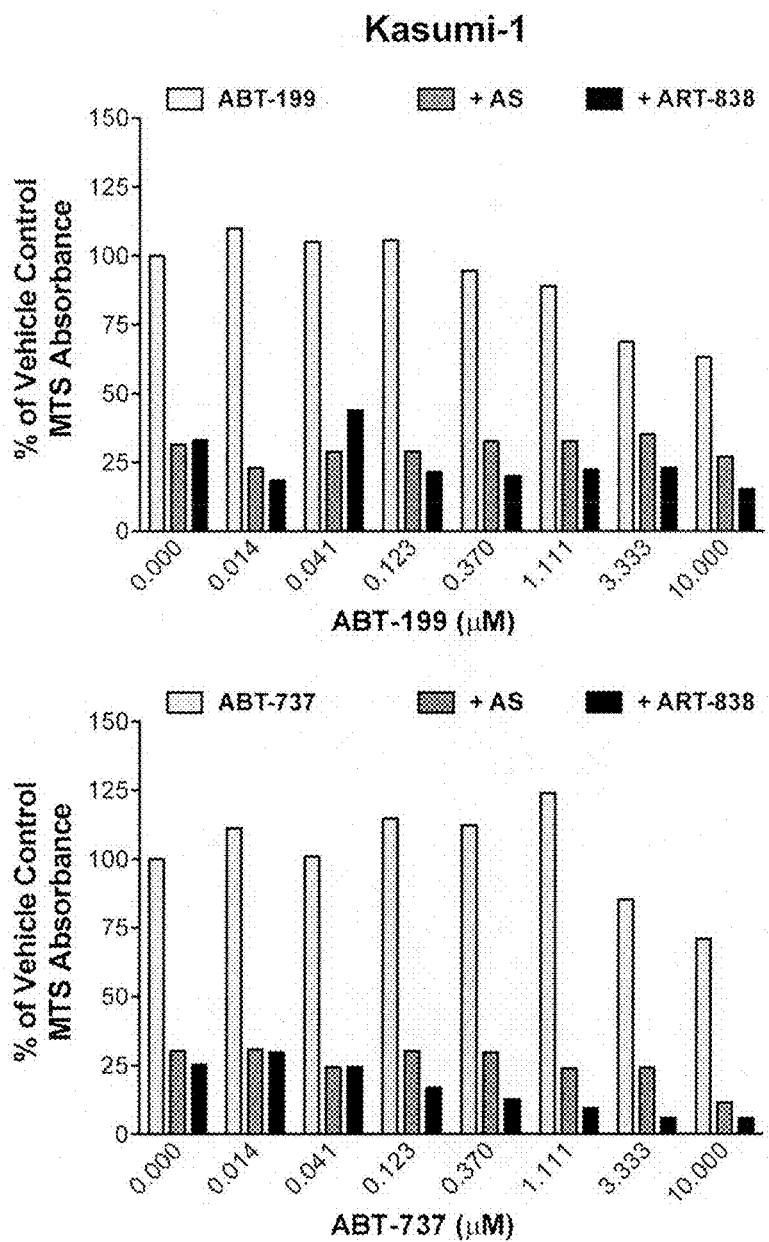
Figure 9C:
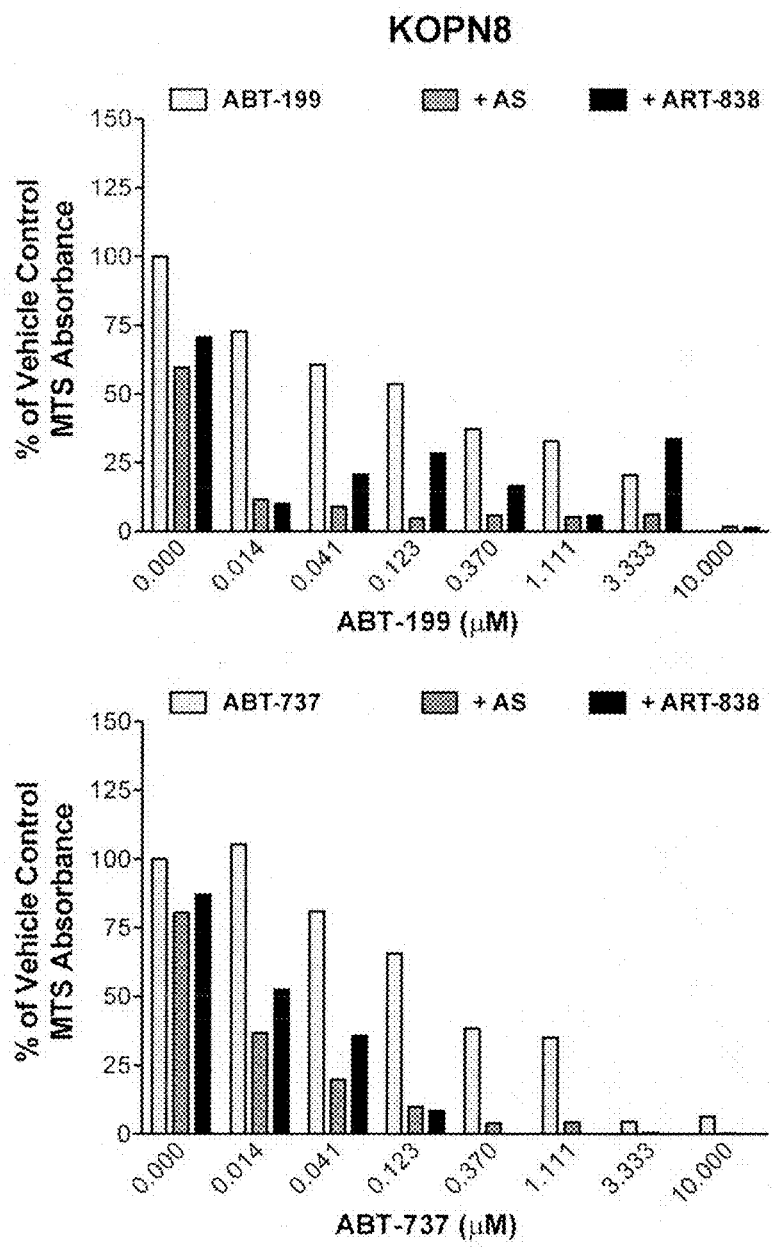
Figure 9D:
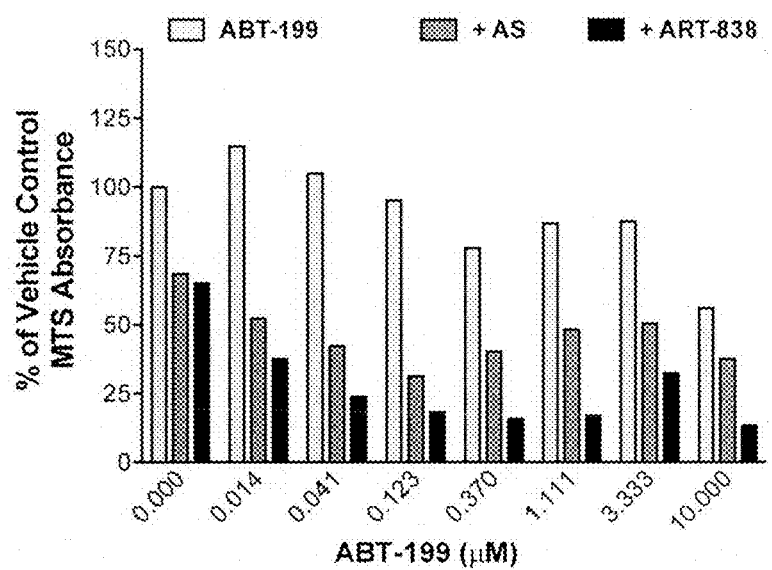
Figure 9D:
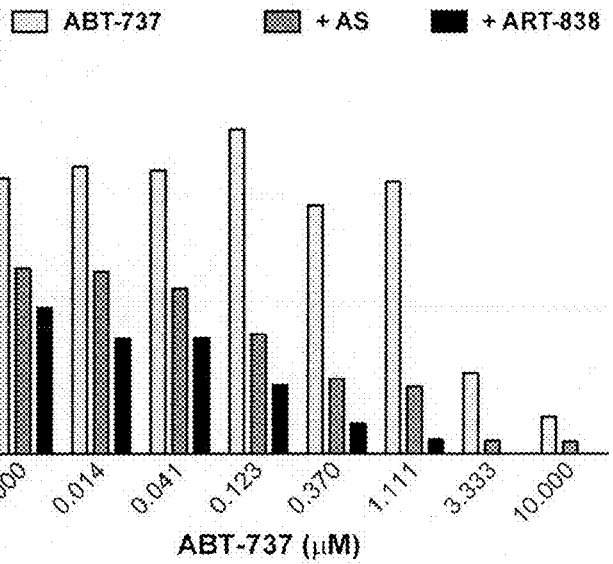
Figure 10A:
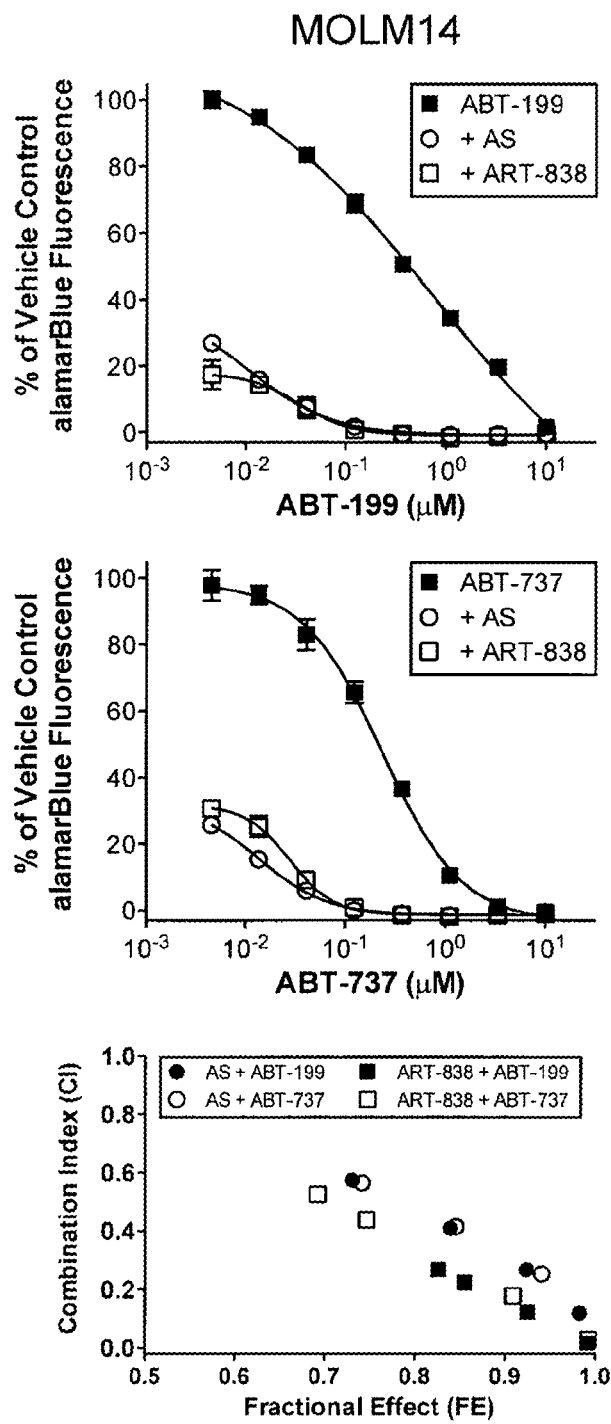
FIGS. 10A-10B. Validation of cytotoxicity of ABT-199/ABT-737+AS/ART-838 combinations by alamarBlue assay. To validate the combined efficacy of two hits from the kinase inhibitor drug combination screen, MOLM14 (FIG. 10A) and KOPN8 (FIG. 10B) cells were treated with increasing concentrations of ABT-199 and ABT-737 with or without AS or ART-838 at their respective $IC_{50}$s (Table 2) for 48h then cytotoxicity was evaluated by alamarBlue assays. Each experiment was performed in triplicate. All data points between 0.1-99.9% growth inhibition were analyzed using the methods of Chou and Talalay [48-50] and combination indices (CIs) calculated. CIs were graphed against the fractional effect (FE; the fraction of cells inhibited at each concentration). CI<1 indicates synergy, CI=1, additivity, CI>1, antagonism.
Figure 10B:
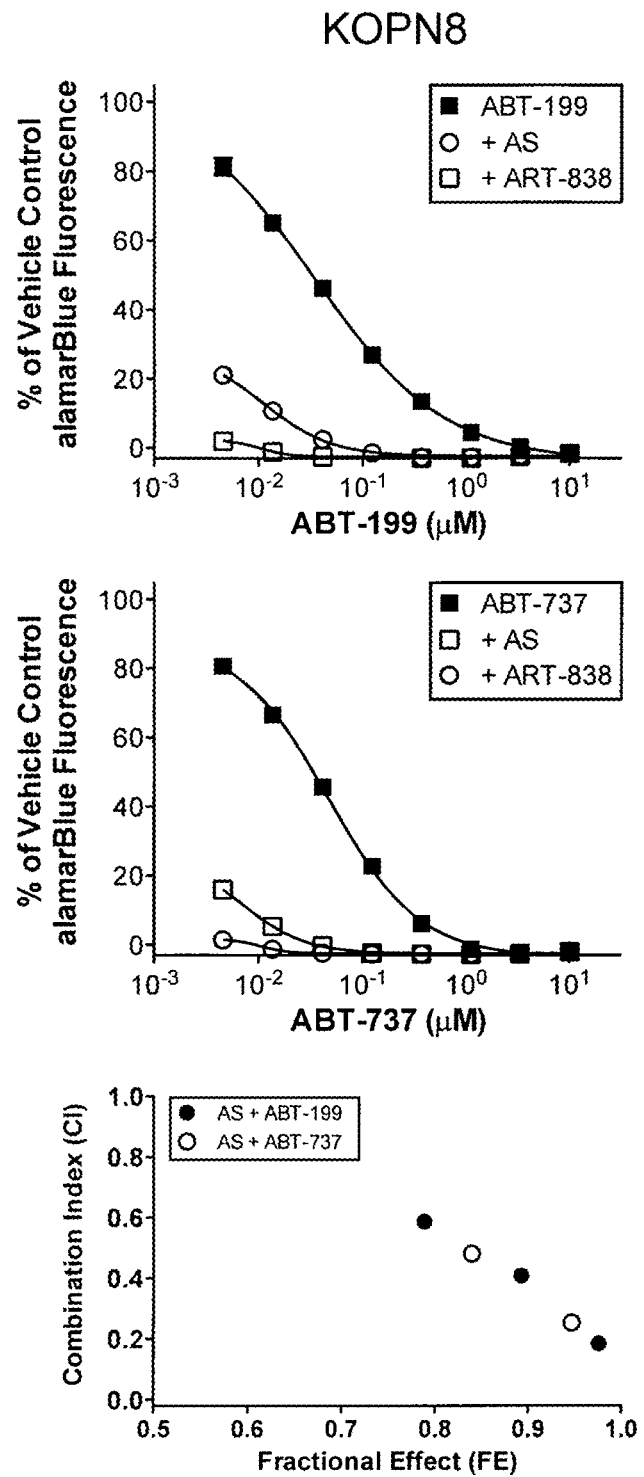
Figure 11A:
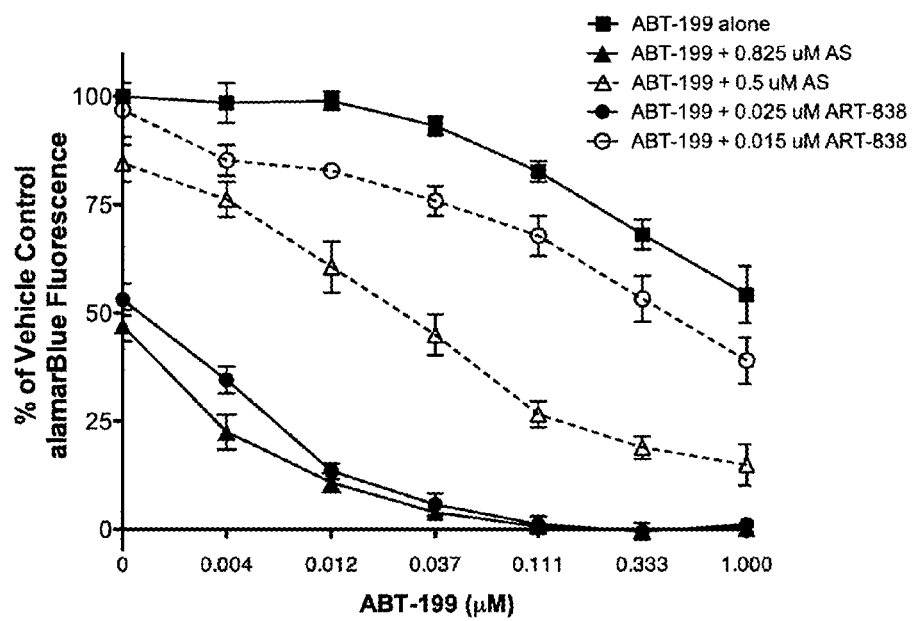
FIGS. 11A-11C. Antileukemic efficacy of ABT-199, ABT-263 or ABT-737 combined with AS or ART-838. MOLM14 cells were treated with increasing concentrations of ABT-199 (FIG. 11A), ABT-263 (FIG. 11B) or ABT-737 (FIG. 11C) without or with AS (0.5 μM or 0.825 μM) or ART-838 (0.015 μM or 0.025 μM) for 48h then cytotoxicity was evaluated by alamarBlue assays. Each experiment was performed in triplicate.
Figure 11B:
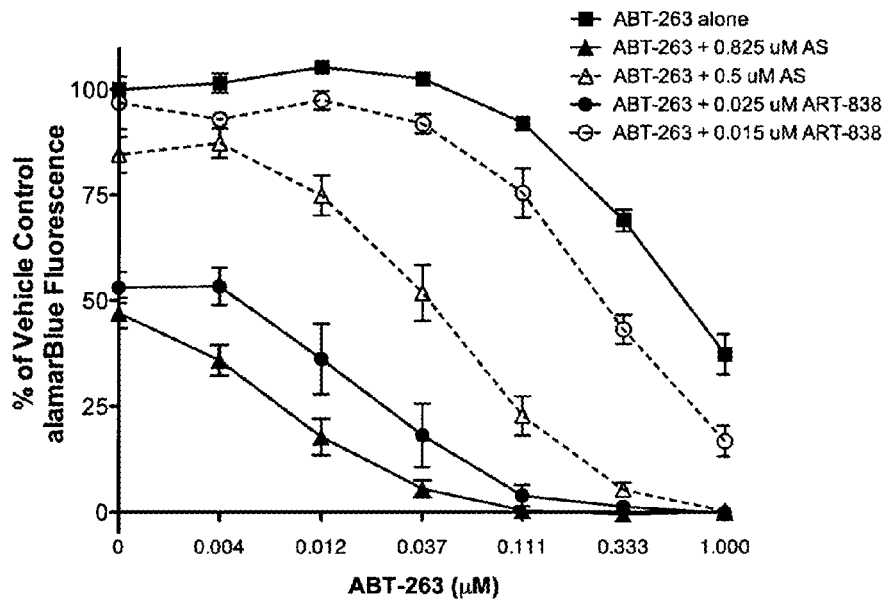
Figure 11C:
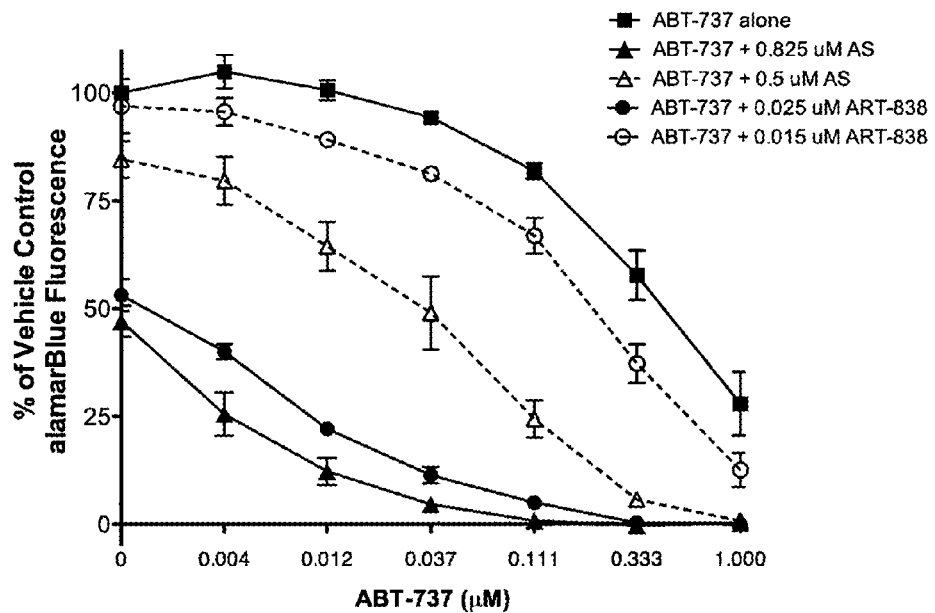
Figure 12:
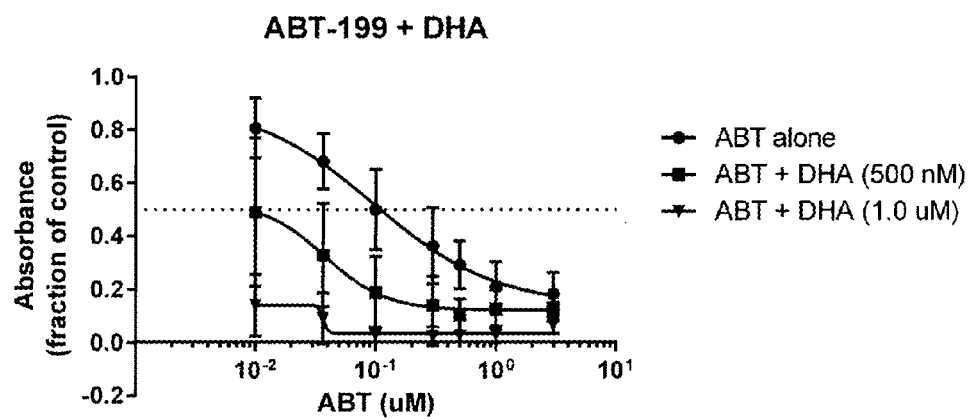
FIG. 12. DHA increased the sensitivity of MOLM14 cells to ABT-199. MOLM14 cells were treated with increasing concentrations of ABT-199, ABT-263 or ABT-737 without or with DHA (500 nM and 1 μM) for 48hrs. Then cytotoxicity was evaluated by alamarBlue assays. Each experiment was performed in triplicate.
Figure 13:
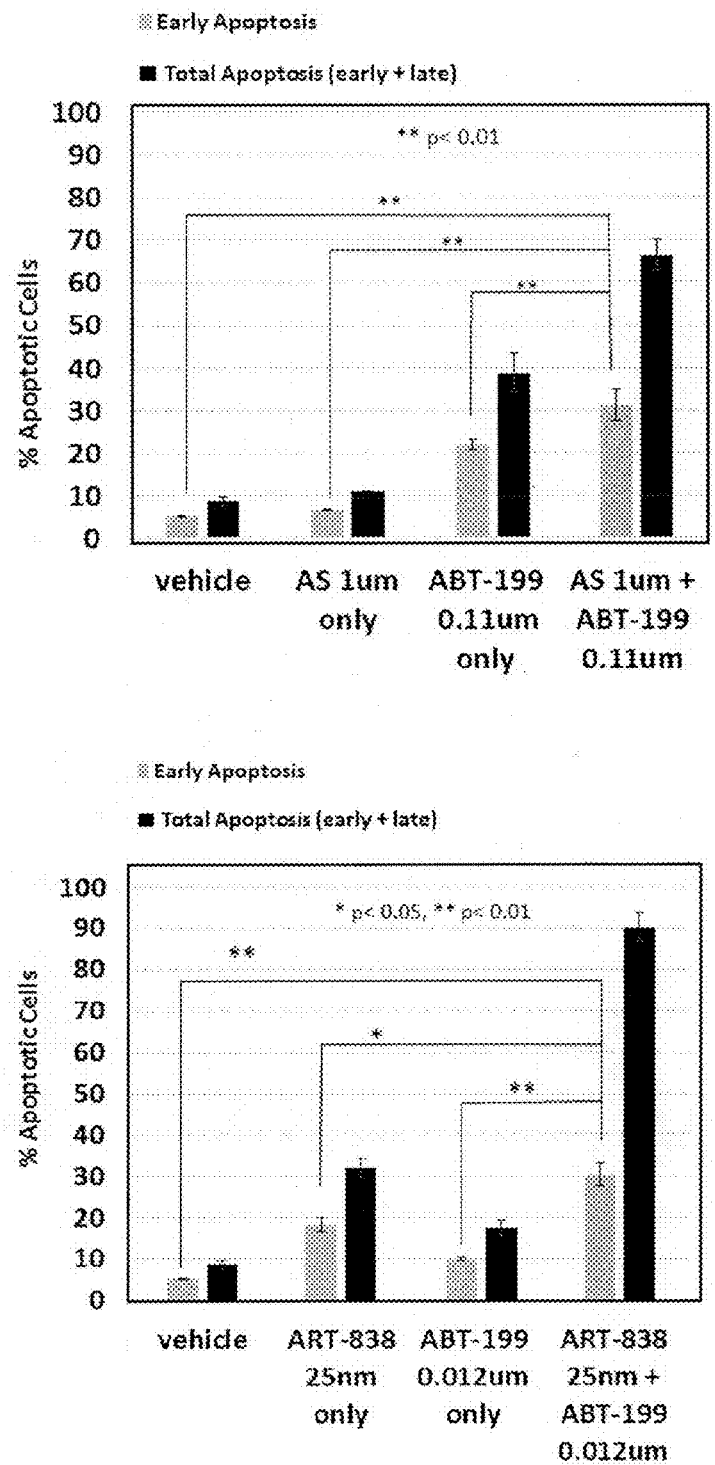
FIG. 13. ABT-199 plus AS or ART-838 cooperated to induce apoptosis. MOLM14 cells were treated with ABT-199 and/or AS (upper panel) or ART-838 (lower panel) for 24 hrs. Cells were stained with APC Annexin-V and 7-AAD and analyzed by fluorescence-activated cell sorting (FACS) to assess apoptotic cells. The early apoptotic population was defined as APC Annexin-V (+) and 7-AAD (−). The total apoptotic population was defined as APC Annexin-V (+). Each experiment was performed in triplicate. Each experiment was performed in triplicate.

Despite previously observed differences in drug combination interactions between AS and ART-838 (FIG. 2, FIG. 3, and [56]), the Bliss differences significantly correlated between AS and ART-838 in all four cell lines in this screen (FIG. 8). A cutoff of 10% inhibition over the Bliss prediction, selected 148 hits: 68 in MOLM14 (including 5 duplicates), one in Kasumi-1, 54 in KOPN8 (including 3 duplicates), and 25 in RCH-ACV. Synergistic drug combinations (hits) were frequently observed in more than one cell line (Table 2). Combinations that were synergistic in at least three cell lines were prioritized for further study, but there were five kinase inhibitors that were hits in both ALL cell lines (KOPN8 and RCH-ACV) and in neither AML cell line (Table 2) and 12 kinase inhibitors that synergized with both AS and ART-838 but only in one cell line (Table 3), suggesting that these combinations may be effective (synergistic) only in particular genetic backgrounds.

TABLE 2

The ranking of top hits from AS/ART-838 + kinase inhibitor library combination drug screen. Drugs from kinase inhibitor library that caused >10% growth inhibition over the Bliss prediction when combined with AS and/or ART-838 in two or more cell lines. Combinations are ordered by the number of cell lines synergistically inhibited by drug 1 combined with AS and/or ART-838, then by the total number of synergistic combinations containing drug 1.

| Drug 1 | Drug 1 target(s) | Drug 2 | Cell line (fractional inhibition over Bliss prediction) | No. Cell Lines |
|---|---|---|---|---|
| ABT-737 | BCL2, BCL2L1, BCL2L2 | AS | MOLM14 (0.50), KOPN8 (0.25), RCH-ACV (0.23) | 4/4 |
|  |  | ART-838 | MOLM14 (0.34), Kasumi-1 (0.11), KOPN8 (0.28), RCH-ACV (0.24) |  |
| GSK-1904529A* | IGF1R, INSR | AS | MOLM14 (0.30, 0.27), KOPN8 (0.18), RCH-ACV (0.20) | 3/4 |
|  |  | ART-838 | MOLM14 (0.57, 0.37), KOPN8 (0.24, 0.16), RCH-ACV (0.14) |  |
| ABT-199 | BCL2 | AS | MOLM14 (0.20), KOPN8 (0.15), RCH-ACV (0.16) | 3/4 |
|  |  | ART-838 | MOLM14 (0.18), KOPN8 (0.11), RCH-ACV (0.35) |  |
| Pazopanib* | KDR, PDGFRB, KIT | ART-838 | MOLM14 (0.17, 0.13), KOPN8 (0.19), RCH-ACV (0.11) | 3/4 |
| Proprietary #8 | ? | ART-838 | MOLM14 (0.10), KOPN8 (0.14), RCH-ACV (0.12) | 3/4 |
| XAV-939 | TNKS, TNKS2 | AS ART-838 | RCH-ACV (0.22) MOLM14 (0.17), KOPN8 (0.18) | 3/4 |
| GW-2580* | CSF1R | AS | MOLM14 (0.25, 0.15), KOPN8 (0.15) | 2/4 |
|  |  | ART-838 | MOLM14 (0.19), KOPN8 (0.19) |  |
| Imatinib | BCR-ABL1, ABL1, ABL2, KIT, PDGFRA, PDGFRB | AS ART-838 | MOLM14 (0.13), KOPN8 (0.20) MOLM14 (0.23), KOPN8 (0.21) | 2/4 |
| JNJ-38877605 | MET | AS | MOLM14 (0.27), KOPN8 (0.12) | 2/4 |
|  |  | ART-838 | MOLM14 (0.17), KOPN8 (0.19) |  |
| NVP-ADW742* | IGF1R | AS | MOLM14 (0.20) | 2/4 |
|  |  | ART-838 | MOLM14 (0.17), KOPN8 (0.27, 0.13) |  |
| S31-201 | STAT3 | AS | MOLM14 (0.30), KOPN8 (0.17) | 2/4 |
|  |  | ART-838 | MOLM14 (0.18), KOPN8 (0.23) |  |
| SU11274 | MET | AS | MOLM14 (0.28), KOPN8 (0.17) | 2/4 |
|  |  | ART-838 | MOLM14 (0.17), KOPN8 (0.39) |  |
| Bortezomib | 20S proteasome | AS | MOLM14 (0.19), RCH-ACV (0.15) | 2/4 |
|  |  | ART-838 | MOLM14 (0.13), RCH-ACV (0.15) |  |
| H-89 | PRKACA | AS | MOLM14 (0.21) | 2/4 |
|  |  | ART-838 | MOLM14 (0.13), KOPN8 (0.10) |  |
| Proprietary #4 | — | AS | MOLM14 (0.22), RCH-ACV (0.10) | 2/4 |
|  |  | ART-838 | MOLM14 (0.20) |  |
| Tivozanib | FLT1, KDR, FLT4, KIT, PDGFRB | AS ART-838 | MOLM14 (0.20), KOPN8 (0.11) KOPN8 (0.22) | 2/4 |
| AGI6780 | mutant IDH2-R140Q | ART-838 | KOPN8 (0.17), RCH-ACV (0.11) | 2/4** |
| CHIR-99021 | GSK3A, GSK3B | AS ART-838 | RCH-ACV (0.15) MOLM14 (0.53) | 2/4 |
| Crizotinib* | ALK, ROS1 | AS ART-838 | RCH-ACV (0.13) KOPN8 (0.12) | 2/4** |
| Erlotinib* | EGFR | AS ART-838 | MOLM14 (0.12) KOPN8 (0.16) | 2/4 |
| K120227 | CSF1R, KDR, PDGFRB, KIT | AS ART-838 | RCH-ACV (0.14) KOPN8 (0.12) | 2/4** |
| Lapatinib* | EGFR, ERBB2 | ART-838 | KOPN8 (0.11), RCH-ACV (0.20) | 2/4** |
| MLN8054 | AURKA | ART-838 | MOLM14 (0.15), KOPN8 (0.11) | 2/4 |
| Proprietary #5 | — | ART-838 | KOPN8 (0.10), RCH-ACV (0.13) | 2/4** |
| Selumetinib | MAP2K1, MAP2K2 | ART-838 | MOLM14 (0.15), KOPN8 (0.19) | 2/4 |
| VX-745 | MAPK14 (p38α) | AS ART-838 | MOLM14 (0.11) KOPN8 (0.14) | 2/4 |

*The library contained duplicate wells of the starred drugs.
**Combinations that were only synergistic in the two ALL cell lines (note: no combinations were synergistic in only the two AML cell lines, likely due to the lack of synergistic combinations in Kasumi-1).

TABLE 3

AS/ART-838-containing drug combinations specific to one cell line. Drugs from kinase inhibitor library that caused >10% growth inhibition over the Bliss prediction when combined with both AS and ART-838 (individually) in only 1 cell line.

| Drug 1 | Drug 1 target(s) | Cell line | Drug 2 | Fractional inhibition over Bliss prediction |
|---|---|---|---|---|
| Sorafenib* | KDR, PDGFRB, RAF, FLT3, KIT | KOPN8 | AS ART-838 | 0.11 0.13, 0.10 |
| Pictilisib* | PIK3CA, PIK3CD | KOPN8 | AS ART-838 | 0.12 0.14 |
| Gefitinib* | EGFR | MOLM14 | AS ART-838 | 0.12 0.16 |
| JAK Inhibitor I | JAK1, JAK2, JAK3 | MOLM14 | AS ART-838 | 0.44 0.15 |
| Linifanib | KDR, CSF1R, FLT1, FLT3, PDGFRB | KOPN8 | AS ART-838 | 0.20 0.19 |
| Motesanib | KDR, FLT4, PDGFRB, KIT | KOPN8 | AS ART-838 | 0.11 0.15 |
| PHT-427 | AKT, PDPK1 | MOLM14 | AS ART-838 | 0.26 0.20 |
| Proprietary #2 | — | MOLM14 | AS ART-838 | 0.26 0.15 |
| Saracatinib | SRC, YES1, FYN, LYN, BLK, FGR, LCK | MOLM14 | AS ART-838 | 0.33 0.21 |
| SB-431542 | TGFBR1, ACVR1B, ACVR1C | MOLM14 | AS ART-838 | 0.16 0.11 |

TABLE 3-continued

AS/ART-838-containing drug combinations specific to one cell line. Drugs from kinase inhibitor library that caused >10% growth inhibition over the Bliss prediction when combined with both AS and ART-838 (individually) in only 1 cell line.

| Drug 1 | Drug 1 target(s) | Cell line | Drug 2 | Fractional inhibition over Bliss prediction |
|---|---|---|---|---|
| Trametinib | MAP2K1, MAP2K2 | KOPN8 | AS | 0.20 |
|  |  |  | ART-838 | 0.20 |
| Vatalanib | FLT1, KDR, FLT4 | KOPN8 | AS | 0.15 |
|  |  |  | ART-838 | 0.12 |

*The library contained duplicate wells of the starred drugs.

The BCL2 Inhibitors ABT-737 and ABT-199 Synergized with AS and ART-838 in at Least 3 of 4 Tested Leukemia Cell Lines Two of the top hits were the BCL2 inhibitors ABT-737 and ABT-199, which synergized with AS and ART-838 in at least 3/4 cell lines (Table 2). Addition of AS or ART-838 enhanced cytotoxicity across the range of concentrations of ABT-199 and ABT-737 (FIG. 9). The combination of ABT-737 plus AS was synergistic in 3/4 cell lines, inhibiting growth by an average of 33% over the Bliss independence prediction; ABT-737 plus ART-838 synergized in 4/4 cell lines with an average of 24% inhibition over the Bliss prediction. ABT-199 plus AS and ABT-199 plus ART-838 synergized in 3/4 cell lines, averaging 17% and 21% inhibition over the Bliss predictions, respectively.

AS/ART-838 Strongly Synergized with ABT-199/ABT-737 in Validation Assays Using alamarBlue to Measure Cytotoxicity and the Chou-Talalay Method to Calculate Combination Interactions To validate the cytotoxic efficacy of AS or ART-838 combined with ABT-199 or ABT-737, MOLM14 and KOPN8 cells were treated with a range of concentrations of ABT-199 or ABT-737 with and without the addition of AS or ART-838 at their respective $IC_{50}$ for 48h. Cytotoxicity of the individual drugs and combinations was assessed using alamarBlue fluorescence, a more sensitive indicator of cell metabolism (as a surrogate for cell number) than MTS. Again, addition of AS or ART-838 potently increased the efficacy of ABT-199 and ABT-737 (FIG. 10A, 10B, 10C, 10D).

Drug combination interactions were assessed using the methods of Chou-Talalay [48-50], a more robust measure of synergy than the Bliss independence model. The Chou-Talalay method, however, can only be used at drug effect levels from 0.1-99.9%. The complete inhibition of MOLM14 and KOPN8 at higher concentrations (or in the case of ABT-199 or ABT-737 plus ART-838 in KOPN8, at all but one tested concentration) left fewer than half the total data points available for drug combination analysis. Analysis of available data points yielded combination indices (CIs) ranging from 0.02-0.59 for these combinations of artemisinins and BCL2 inhibitors, indicating robust synergy across all tested concentrations and combinations (FIG. 10E, 10F; CI<1 indicates synergy, CI=1, additivity, CI>1, antagonism).

Discussion #2

This drug combination screen identified potently synergistic antileukemic interactions between artemisinins (AS and ART-838) and BCL2 inhibitors (ABT-199 and ABT-737). Drug substitution experiments, in which another drug with the same targets is tested in place of the drug hit, are often used to verify that the synergistic effects of a drug combination are due to an on-target effect [41,43]. Since both ABT-199 and ABT-737 are BCL2 family inhibitors, the validation of each serves as a drug substitution validation for the other, strongly suggesting that inhibition of BCL2 synergizes with the artemisinins, AS and ART-838.

Results #3

ART-838 Enhanced In Vivo Efficacy of ARA Against Acute Leukemia Xenografts in NSG Mice.

Figure 14:
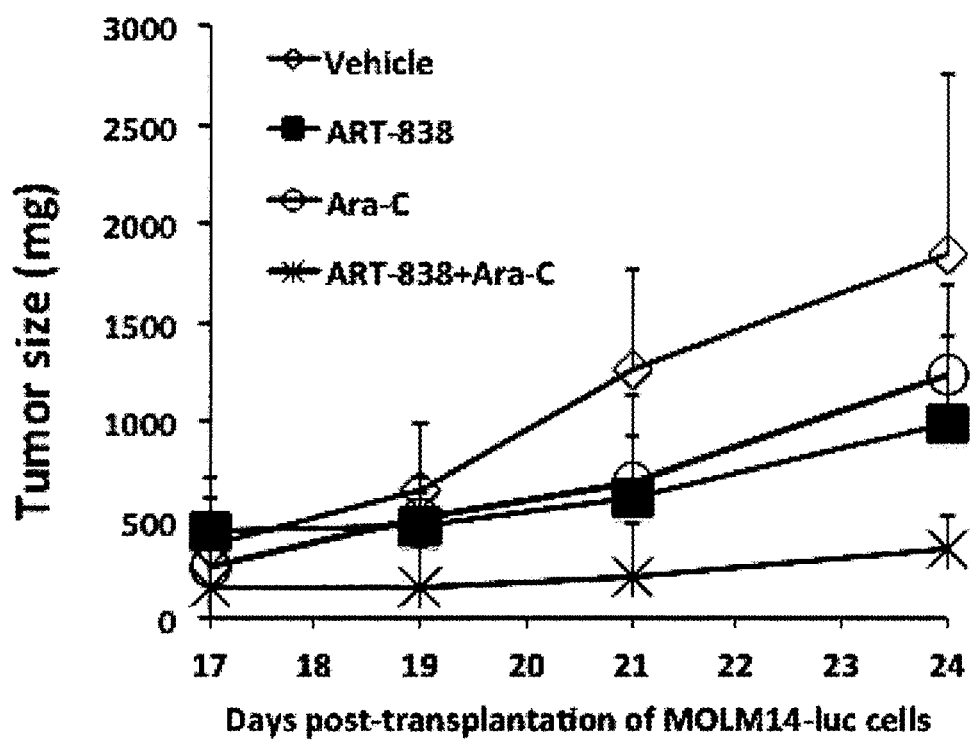
FIG. 14. ART-838 enhanced in vivo efficacy of ARA against acute leukemia xenografts in NSG mice. NSG mice transplanted subcutaneously with luciferase labeled MOLM14 (MOLM14-luc) AML cells, were treated with vehicle, ARA ("Ara-C"), ART-838 or ART-838 plus ARA starting on day 17 after transplantation. Ara-C (40 mg/kg/d) was given i.p. on day 17, 18, 19, 20, 21 and 24. ART-838 (200 mg/kg/d) was given p.o. on day 17, 20 and 24. Mouse tumors were measured on the indicated days.

The anti-leukemic efficacy of ART-838 plus ARA was tested in NSG mice transplanted subcutaneously with luciferase labeled MOLM14 (MOLM14-luc) AML cells. Palpable tumors (approximately 100 mg tumor mass) appeared in mice about 2 weeks after transplantation. Mice were then treated with vehicle, ARA, ART-838 or ART-838 plus ARA as indicated in FIG. 14. Mouse tumors were measured with calipers on the indicated days. Based on tumor size determined on day 24 (FIG. 14), the combination of ARA plus ART-838 inhibited tumor growth substantially more than did either drug alone.

AS Enhanced In Vivo Efficacy of SOR Against Acute Leukemia Xenografts in NSG Mice.

Figure 15:
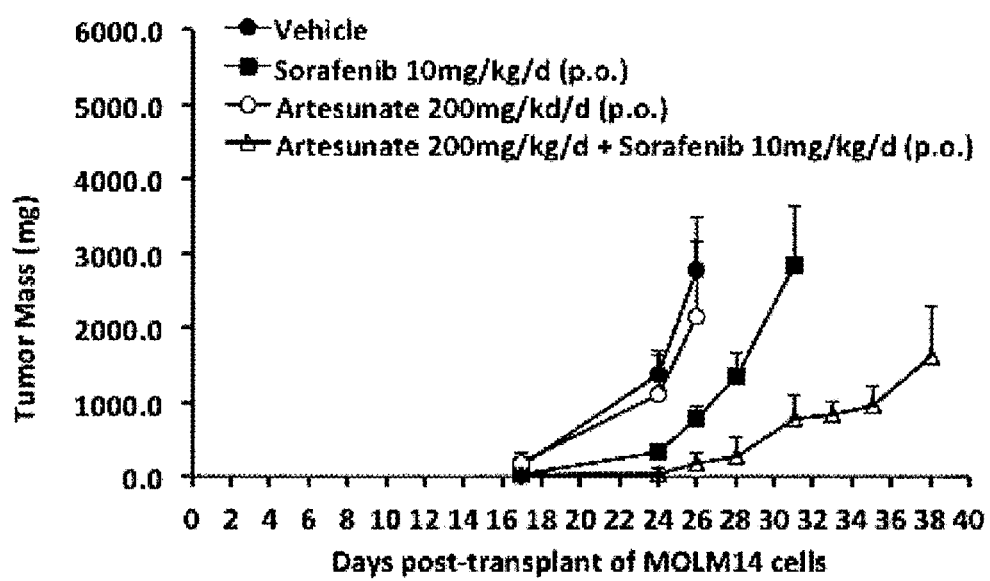
FIG. 15. AS enhanced in vivo efficacy of Sorafenib (SOR) against acute leukemia xenografts in NSG mice. NSG mice transplanted subcutaneously with MOLM14 AML cells, were treated with vehicle, SOR, AS or SOR plus AS as indicated starting on day 3 after transplantation. Drug or vehicle were given p.o. on day 3-7, 17-21, and 31-35 when possible. Mouse tumors were measured on the indicated days.

The anti-leukemic effect of AS plus SOR was tested in NSG mice transplanted subcutaneously with MOLM14 AML cells. Mice were treated with vehicle, SOR, AS or AS plus SOR as indicated in FIG. 14. Palpable tumors appeared about 2 weeks after transplantation. Based on tumor size determined on day 24 (FIG. 15), the combination of the AS plus SOR inhibited tumor growth substantially more than did either drug alone.

Discussion #3

Potent in vivo antileukemic efficacy was identified for combinations of AS or ART-838 with ARA or SOR.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Misaghian, N., et al., *Targeting the leukemic stem cell: the Holy Grail of leukemia therapy*. Leukemia, 2009. 23(1): p. 25-42.
2. Warner, J. K., et al., *Concepts of human leukemic development*. Oncogene, 2004. 23(43): p. 7164-77.
3. Brown, P., et al., *Combinations of the FLT3 inhibitor CEP-701 and chemotherapy synergistically kill infant and childhood MLL-rearranged ALL cells in a sequence-dependent manner*. Leukemia, 2006. 20(8): p. 1368-76.
4. Grunwald, M. R. and M. J. Levis, *FLT3 inhibitors for acute myeloid leukemia: a review of their efficacy and mechanisms of resistance*. Int J Hematol, 2013. 97(6): p. 683-94.
5. Levis, M., et al., *In vitro studies of a FLT3 inhibitor combined with chemotherapy: sequence of administration is important to achieve synergistic cytotoxic effects*. Blood, 2004. 104(4): p. 1145-50.
6. Miller, L. H. and X. Su, *Artemisinin: discovery from the Chinese herbal garden*. Cell, 2011. 146(6): p. 855-8.

7. *Antimalaria studies on Qinghaosu.* Chin Med J (Engl), 1979. 92(12): p. 811-6.
8. Ho, W. E., et al., *Artemisinins: pharmacological actions beyond anti-malarial.* Pharmacol Ther, 2014. 142(1): p. 126-39.
9. Mott, B. T., et al., *Artemisinin-derived dimer phosphate esters as potent anti-cytomegalovirus (anti-CMV) and anti-cancer agents: a structure-activity study.* Bioorg Med Chem, 2013. 21(13): p. 3702-7.
10. Crespo-Ortiz, M. P. and M. Q. Wei, *Antitumor activity of artemisinin and its derivatives: from a well-known anti-malarial agent to a potential anticancer drug.* J Biomed Biotechnol, 2012. 2012: p. 247597.
11. Slack, R. D., A. M. Jacobine, and G. H. Posner, *Antimalarial peroxides: advances in drug discovery and design.* Medchemcomm, 2012. 3(1): p. 281-297.
12. Eckstein-Ludwig, U., et al., *Artemisinins target the SERCA of Plasmodium falciparum.* Nature, 2003. 424 (6951): p. 957-61.
13. Arav-Boger, R., et al., *Artemisinin-derived dimers have greatly improved anti-cytomegalovirus activity compared to artemisinin monomers.* PLoS One, 2010. 5(4): p. e10370.
14. Woerdenbag, H. J., et al., *Cytotoxicity of artemisinin-related endoperoxides to Ehrlich ascites tumor cells.* J Nat Prod, 1993. 56(6): p. 849-56.
15. Posner, G. H., et al., *Orally active, antimalarial, anticancer, artemisinin-derived trioxane dimers with high stability and efficacy.* J Med Chem, 2003. 46(6): p. 1060-5.
16. Paik, I. H., et al., *Second generation, orally active, antimalarial, artemisinin-derived trioxane dimers with high stability, efficacy, and anticancer activity.* J Med Chem, 2006. 49(9): p. 2731-4.
17. D'Angelo, J. G., et al., *Artemisinin derivatives inhibit Toxoplasma gondii in vitro at multiple steps in the lytic cycle.* J Antimicrob Chemother, 2009. 63(1): p. 146-50.
18. Posner, G. H., et al., *Trioxane dimers have potent antimalarial, antiproliferative and antitumor activities in vitro.* Bioorg Med Chem, 1997. 5(7): p. 1257-65.
19. Posner, G. H., et al., *Antimalarial, antiproliferative, and antitumor activities of artemisinin-derived, chemically robust, trioxane dimers.* J Med Chem, 1999. 42(21): p. 4275-80.
20. Posner, G. H., et al., *New chemical and biological aspects of artemisinin-derived trioxane dimers.* Bioorg Med Chem, 2002. 10(1): p. 227-32.
21. Posner, G. H., et al., *Anticancer and antimalarial efficacy and safety of artemisinin-derived trioxane dimers in rodents.* J Med Chem, 2004. 47(5): p. 1299-301.
22. He, R., et al., *An artemisinin-derived dimer has highly potent anti-cytomegalovirus (CMV) and anti-cancer activities.* PLoS One, 2011. 6(8): p. e24334.
23. Chaturvedi, D., et al., *Artemisinin and its derivatives: a novel class of anti-malarial and anti-cancer agents.* Chem Soc Rev, 2010. 39(2): p. 435-54.
24. Rosenthal, A. S., et al., *Malaria-infected mice are cured by a single oral dose of new dimeric trioxane sulfones which are also selectively and powerfully cytotoxic to cancer cells.* J Med Chem, 2009. 52(4): p. 1198-203.
25. Alagbala, A. A., et al., *Biological mechanisms of action of novel C-10 non-acetal trioxane dimers in prostate cancer cell lines.* J Med Chem, 2006. 49(26): p. 7836-42.
26. Jeyadevan, J. P., et al., *Antimalarial and antitumor evaluation of novel C-10 non-acetal dimers of 10beta-(2-hydroxyethyl)deoxoartemisinin.* J Med Chem, 2004. 47(5): p. 1290-8.
27. Efferth, T., et al., *The anti-malarial artesunate is also active against cancer.* Int J Oncol, 2001. 18(4): p. 767-73.
28. Dell'Eva, R., et al., *Inhibition of angiogenesis in vivo and growth of Kaposi's sarcoma xenograft tumors by the anti-malarial artesunate.* Biochem Pharmacol, 2004. 68(12): p. 2359-66.
29. Efferth, T., et al., *Artesunate induces ROS-mediated apoptosis in doxorubicin-resistant T leukemia cells.* PLoS One, 2007. 2(8): p. e693.
30. Keiser, J. and J. Utzinger, *Artemisinins and synthetic trioxolanes in the treatment of helminth infections.* Curr Opin Infect Dis, 2007. 20(6): p. 605-12.
31. El Zawawy, L. A., *Effect of artesunate on Toxoplasma gondii: in vitro and in vivo studies.* J Egypt Soc Parasitol, 2008. 38(1): p. 185-201.
32. Du, J. H., et al., *Artesunate induces oncosis-like cell death in vitro and has antitumor activity against pancreatic cancer xenografts in vivo.* Cancer Chemother Pharmacol, 2010. 65(5): p. 895-902.
33. Ma, H., et al., *The effects of artesunate on the expression of EGFR and ABCG2 in A549 human lung cancer cells and a xenograft model.* Molecules, 2011. 16(12): p. 10556-69.
34. Xu, Q., et al., *Artesunate inhibits growth and induces apoptosis in human osteosarcoma HOS cell line in vitro and in vivo.* J Zhejiang Univ Sci B, 2011. 12(4): p. 247-55.
35. Zhou, X., et al., *Artesunate inhibits the growth of gastric cancer cells through the mechanism of promoting oncosis both in vitro and in vivo.* Anticancer Drugs, 2013. 24(9): p. 920-7.
36. Jin, M., et al., *In vivo study of effects of artesunate nanoliposomes on human hepatocellular carcinoma xenografts in nude mice.* Drug Deliv, 2013. 20(3-4): p. 127-33.
37. Hooft van Huijsduijnen, R., et al., *Anticancer properties of distinct antimalarial drug classes.* PLoS One, 2013. 8(12): p. e82962.
38. Zhang, Z. Y., et al., *[Artesunate combined with vinorelbine plus cisplatin in treatment of advanced non-small cell lung cancer: a randomized controlled trial].* Zhong Xi Yi Jie He Xue Bao, 2008. 6(2): p. 134-8.
39. Holohan, C., et al., *Cancer drug resistance: an evolving paradigm.* Nat Rev Cancer, 2013. 13(10): p. 714-26.
40. Crystal, A. S., et al., *Patient-derived models of acquired resistance can identify effective drug combinations for cancer.* Science, 2014. 346(6216): p. 1480-6.
41. Axelrod, M., et al., *Combinatorial drug screening identifies compensatory pathway interactions and adaptive resistance mechanisms.* Oncotarget, 2013. 4(4): p. 622-35.
42. Axelrod, M., et al., *Combinatorial drug screening identifies synergistic co-targeting of Bruton's tyrosine kinase and the proteasome in mantle cell lymphoma.* Leukemia, 2014. 28(2): p. 407-10.
43. Roller, D. G., et al., *Synthetic lethal screening with small-molecule inhibitors provides a pathway to rational combination therapies for melanoma.* Mol Cancer Ther, 2012. 11(11): p. 2505-15.
44. Tyner, J. W., et al., *Kinase pathway dependence in primary human leukemias determined by rapid inhibitor screening.* Cancer Res, 2013. 73(1): p. 285-96.
45. Tanavde, V. M., et al., *Human stem progenitor cells from neonatal cord blood have greater hematopoietic expansion capacity than those from mobilized adult blood.* Exp Hematol, 2002. 30(7): p. 816-23.

46. Pozarowski, P. and Z. Darzynkiewicz, *Analysis of cell cycle by flow cytometry*. Methods Mol Biol, 2004. 281: p. 301-11.
47. Vermes, I., et al., *A novel assay for apoptosis. Flow cytometric detection of phosphatidylserine expression on early apoptotic cells using fluorescein labelled Annexin V*. J Immunol Methods, 1995. 184(1): p. 39-51.
48. Chou, T. C., *Theoretical basis, experimental design, and computerized simulation of synergism and antagonism in drug combination studies*. Pharmacol Rev, 2006. 58(3): p. 621-81.
49. Chou, T. C. and P. Talalay, *Quantitative analysis of dose-effect relationships: the combined effects of multiple drugs or enzyme inhibitors*. Adv Enzyme Regul, 1984. 22: p. 27-55.
50. Chou, T. C., *Drug combination studies and their synergy quantification using the Chou-Talalay method*. Cancer Res, 2010. 70(2): p. 440-6.
51. Bliss, C., *The toxicity of poisons applied jointly*. Ann Appl Biol, 1939. 26: p. 585-615.
52. Pham, N. A. and D. W. Hedley, *Respiratory chain-generated oxidative stress following treatment of leukemic blasts with DNA-damaging agents*. Exp Cell Res, 2001. 264(2): p. 345-52.
53. Gorrini, C., I. S. Harris, and T. W. Mak, *Modulation of oxidative stress as an anticancer strategy*. Nat Rev Drug Discov, 2013. 12(12): p. 931-47.
54. Hu, S., et al., *Activity of the multikinase inhibitor sorafenib in combination with cytarabine in acute myeloid leukemia*. J Natl Cancer Inst, 2011. 103(11): p. 893-905.
55. Sallmyr, A., et al., *Internal tandem duplication of FLT3 (FLT3/ITD) induces increased ROS production, DNA damage, and misrepair: implications for poor prognosis in AML*. Blood, 2008. 111(6): p. 3173-82.
56. Cai, H., et al., *In vitro combination of anti-cytomegalovirus compounds acting through different targets: role of the slope parameter and insights into mechanisms of Action*. Antimicrob Agents Chemother, 2014. 58(2): p. 986-94.
57. Liu, L., L. F. Zuo, and J. W. Guo, *Reversal of multidrug resistance by the anti-malaria drug artesunate in the esophageal cancer Eca109/ABCG2 cell line*. Oncol Lett, 2013. 6(5): p. 1475-1481.
58. Dong, H. Y. and Z. F. Wang, *Antitumor effects of artesunate on human breast carcinoma MCF-7 cells and IGF-IR expression in nude mice xenografts*. Chin J Cancer Res, 2014. 26(2): p. 200-7.
59. Liu, Y. and Y. F. Cui, *Synergism of cytotoxicity effects of triptolide and artesunate combination treatment in pancreatic cancer cell lines*. Asian Pac J Cancer Prev, 2013. 14(9): p. 5243-8.
60. Sieber, S., et al., *Combination treatment of malignant B cells using the anti-CD20 antibody rituximab and the anti-malarial artesunate*. Int J Oncol, 2009. 35(1): p. 149-58.
61. Deng, X., et al., *Bcl2 retards G1/S cell cycle transition by regulating intracellular ROS*. Blood, 2013. 102(9): p. 3179-3185.
62. Chong, S. J. F., et al., *Mitochondrial ROS and involvement of Bcl-2 as a mitochondrial ROS regulator*. Science, 2014. 19(A):p. 39-48.
63. Mott, B. T., et al., *Artemisinin-derived dimer phosphate esters as potent anti-cytomegalovirus (anti-CMV) and anti-cancer agents: a structure-activity study*. Bioorg Med Chem. 2013. 21: p. 3702-3707.
64. Hollingshead, M. *Intraperitoneal and subcutaneous tumor models for assessing anti-neoplastic agents in rodents*. Curr Protoc Pharmacol, 2002. Ch. 5, Unit 5.28.

What is claimed is:

1. A method of treating cancer in a subject, comprising administering therapeutically effective amounts of an artemisinin and a second agent to a subject having cancer,
   wherein the cancer is selected from the group consisting of acute myeloid leukemia (AML), acute lymphoid leukemia (ALL), B cell ALL (B-ALL), T cell ALL (T-ALL), and
   wherein the artemisinin is artesunate (AS) and the second agent is ABT-737;
   wherein the artemisinin is AS and the second agent is ABT-199;
   wherein the artemisinin is AS and the second agent is cytarabine (ARA);
   wherein the artemisinin is AS and the second agent is doxorubicin (DOX);
   wherein the artemisinin is AS and the second agent is etoposide (ETO);
   wherein the artemisinin is ART-838 and the second agent is ABT-737;
   wherein the artemisinin is ART-838 and the second agent is ABT-199;
   wherein the artemisinin is ART-838 and the second agent is ARA;
   wherein the artemisinin is ART-838 and the second agent is DOX;
   wherein the artemisinin is ART-838 and the second agent is ETO;
   wherein the artemisinin is ART-838 and the second agent is midostaurin (MID);
   wherein the artemisinin is ART-838 and the second agent is lestaurtinib (LES); or
   wherein the artemisinin is ART-838 and the second agent is sorafenib (SOR),
   wherein the combination of the artemisinin and the second agent have a synergistic therapeutic effect on the cancer.

2. The method of claim 1, wherein the artemisinin and the second agent are administered in either order, sequentially or concurrently, with overlapping or non-overlapping periods of administration.

3. The method of claim 2, comprising concurrently administering therapeutically effective amounts of an artemisinin and a second agent to a subject having cancer.

4. The method of claim 2, comprising sequentially administering therapeutically effective amounts of an artemisinin and a second agent to a subject having cancer.

5. The method of claim 1, wherein the artemisinin and the second agent are formulated, separately or together, in pharmaceutical compositions comprising a pharmaceutically acceptable carrier or diluent.

6. The method of claim 1, wherein the therapeutically effective amount of the artemisinin is between about 0.1 and 100 mg/kg body weight of the subject.

7. The method of claim 1, wherein the therapeutically effective amount of the secondary agent is between about 0.1 and 100 mg/kg body weight of the subject.

* * * * *